United States Patent [19]

Kaplan et al.

[11] 4,359,476

[45] Nov. 16, 1982

[54] ADJACENTLY SUBSTITUTED CYCLOALKANE-AMIDE ANALGESICS

[75] Inventors: Lester J. Kaplan, Kalamazoo; Moses W. McMillan, Portage; Jacob Szmuszkovicz, Kalamazoo, all of Mich.

[73] Assignee: The Upjohn Company, Kalamazoo, Mich.

[21] Appl. No.: 252,536

[22] Filed: Apr. 9, 1981

[51] Int. Cl.$^3$ .................. C07D 487/00; A61K 31/40
[52] U.S. Cl. .................................. 424/274; 548/407;
549/39; 549/333; 260/330.3; 546/15; 546/230;
546/231; 546/234; 424/244; 424/267; 424/275;
424/278; 424/304; 424/309; 424/311; 424/324;
564/155; 564/162; 564/163; 564/166; 560/16;
560/251
[58] Field of Search ........... 260/326.4, 326.35, 326.36,
260/239 A, 340.9 R, 465 E, 340.7, 330.3;
424/274, 244, 267, 275, 278, 304, 309, 311, 324;
549/39; 546/15, 230, 231, 234; 564/162, 163,
166, 155; 560/16, 251

[56] References Cited

U.S. PATENT DOCUMENTS

| | | | |
|---|---|---|---|
| 3,510,492 | 5/1970 | Szmuszkovicz | 546/232 |
| 4,065,573 | 12/1977 | Lednicer | 424/278 |
| 4,098,904 | 7/1978 | Szmuskovicz | 424/324 |
| 4,145,435 | 3/1979 | Szmuszkovicz | 424/274 |
| 4,156,733 | 5/1979 | Szmuszkovicz | 260/326.4 |
| 4,212,878 | 7/1980 | Lednicer et al. | 424/274 |

*Primary Examiner*—Jane T. Fan
*Attorney, Agent, or Firm*—John T. Reynolds

[57] ABSTRACT

N-[2-Amino(oxy or thio group) substituted-cycloaliphatic]phenylacetamide and -benzamide compounds, having the oxy- or thio group substituents on a cycloaliphatic ring carbon adjacent to either of the nitrogen bearing carbons of the cycloaliphatic ring, e.g., cis- and trans-4-bromo-N-[3-methoxy-2-(1-pyrrolidinyl)cyclohexyl]-N-methylbenzamide, and trans-3,4-dichloro-N-methyl-N-[7-(1-pyrridolinyl)-1,4-dioxaspiro[4.5]dec-6-yl]benzeneacetamide, and salts thereof, have useful analgesic activity and low abuse liability in humans and valuable warm blooded animals. Processes for their production and pharmaceutical compositions and method of use are also disclosed.

20 Claims, No Drawings

ADJACENTLY SUBSTITUTED CYCLOALKANE-AMIDE ANALGESICS

INTRODUCTION

This invention relates to N-[2-amino(oxy or thio group substituted)-cycloaliphatic]phenylacetamide and -benzamide compounds. More particularly, this invention provides some new N-[2-amino-(adjacently-oxy-group-substituted)-cycloaliphatic]phenylacetamide and -benzamide compounds which have useful analgesic activity and low abuse liability, or which are useful as chemical intermediates to such useful compounds. Processes for their preparation are disclosed. Pharmaceutical compositions and methods of use are also provided.

BACKGROUND OF THE INVENTION

Szmuszkovicz U.S. Pat. No. 4,145,435 discloses some cis- and trans-N-(2-aminocycloaliphatic)-2-arylacetamide derivative compounds, e.g., N-[2-(N',N'-dimethylamino)cyclohexyl]-N-methyl-2-(4-bromophenyl)acetamide and trans-N-methyl-N-[2-(1-pyrrolidinyl)-cyclohexyl]-2-(3,4-dichlorophenyl)acetamide, which have potent analgesic activity; the preferred compounds thereof have, in addition, only low to moderate apparent physical dependence liability compared to morphine and methadone. That Szmuszkovicz U.S. Pat. No. 4,145,435 also describes some prior art patent and publication background that may be of interest herein also.

Also, Szmuszkovicz U.S. Pat. No. 4,098,904 discloses some cis- and trans-N-(2-aminocycloaliphatic)benzamide compounds, e.g., N-methyl-N-(2-aminocycloaliphatic)benzamide compounds, e.g., N-methyl-N-[2-(1-pyrrolidinyl)cyclohexyl]-3,4-dichlorobenzamide which have potent analgesic activity, making them useful for relieving pain in warm-blooded animals. That U.S. Pat. No. 4,098,904 also discloses background patents and publications which may be of interest herein.

Lednicer U.S. Pat. No. 4,212,878 discloses some N-[(1-amino-4-(mono- or di-oxygen group substituted)cyclohexyl)methyl]benzeneacetamide derivatives, e.g., 2-(3,4-dichlorophenyl)-N[8-(1-pyrrolidinyl)1,4-dioxaspiro[4.5]dec-8-yl)methyl]acetamide, which also have analgesic drug properties with lower physical dependence liability characteristics than morphine or methadone. That Lednicer patent also refers to what is now Lednicer U.S. Pat. No. 4,065,573 which discloses some 4-amino-4-phenylcyclohexanone ketal compounds, e.g., 4-(m-hydroxyphenyl)-4-(dimethylamino)cyclohexanone ethylene ketal and 4-(m-hydroxyphenyl)4-(n-butylmethylamino]cyclohexanone ethylene ketal, which are useful for relieving pain in animals, some of which compounds exhibit narcotic antagonist activity.

Other references are listed in the accompanying prior art statement.

Some concern has been expressed about possible dysphoric side effects of some of these prior art compounds when used as analgesic drugs. Those skilled in the art continue to search for new and more advantageous analgesic compounds.

OBJECTS OF THE INVENTION

It is an object of the invention to provide some new adjacently substituted N-(oxy or thio group substituted)-2-(aminocycloaliphatic)benzeneacetamide and -benzamide compounds which are useful as analgesic compounds or as chemical intermediates to analgesic compounds.

It is a further object of this invention to provide these new compounds of the above type which have useful analgesic properties, only low to moderate physical dependence liability compared to the high physical dependence liability of morphine and methadone and, hopefully also, less dysporia inducing properties than prior known analgesic compounds.

Other objects, aspects, and advantages of this invention will become apparent from reading and remaining specification and claims which follow.

SUMMARY OF THE INVENTION

Briefly, this invention provides some new 2-aminocycloaliphaticbenzene-acetamide and -benzamide compounds bearing oxy- or thio- group substituents on a cycloaliphatic ring carbon adjacent to either of the nitrogen bearing carbons of that cycloaliphatic ring, e.g., cis- and trans-4-bromo-N-[3-methoxy-2-(1-pyrrolidinyl)cyclohexyl]-N-methylbenzamide and cis- and trans-3,4-dichloro-N-methyl-N-[7-(1-pyrrolidinyl)-1,4-dioxaspiro[4.5]dec-6-yl]benzeneacetamide, and salts thereof, which have been found to have useful ranges of analgesic properties while also having low apparent physical dependence liability, and which also, hopefully, have reduced dysphoria inducing properties. This invention also includes compounds of the above general type which may exhibit some analgesic activity of their own, but which are of more importance as chemical intermediates for the preparation of more advantageous analgesic drug compounds included herein. This invention also includes pharmaceutical compositions containing these compounds as an active analgesic component and the method of inducing analgesic activity in an animal patient, including humans, by administering one of these new compounds in an amount effective and sufficient to induce analgesic activity, regardless of pain origin, e.g., traumatic pain, bone pain, cancer pain, postsurgical pain, homotopic pain, menstrual pain, headache, and the like. The invention also relates to new compounds in pharmaceutical dosage unit forms to be used, hopefully more advantageously, for the relief of pain in valuable animals and human patients suffering pain.

DETAILED DESCRIPTION OF THE INVENTION

More particularly, this invention provides some new compounds having a chemical structure of Formula I below wherein p and n are each integers independently selected from the group 0, 2, 3 and 4 so that the resulting cycloaliphatic ring of Formula I has from 5 to 7 ring carbon atoms, inclusive, and the $R_3$ and $R_4$ bearing carbon is adjacent to one of the two nitrogen bearing carbons of that cycloaliphatic ring.

In detail, the compounds of this invention are those of the Formula I wherein R is hydrogen or $C_1$ to $C_3$-alkyl;

$R_1$ and $R_2$, taken separately, are each hydrogen or $C_1$ to $C_3$-alkyl;

$R_1$ and $R_2$, taken together with the nitrogen to which they are bonded are azetidinyl, pyrrolidinyl or piperidinyl;

$R_3$, taken separately, is hydroxy, $C_1$ to $C_2$-alkyloxy or $C_1$ to $C_3$-alkanoyloxy;

$R_4$, taken separately, is hydrogen when $R_3$ is hydroxy, $C_1$ to $C_2$-alkyloxy, or $C_1$ to $C_3$-alkanoyloxy;

$R_3$ and $R_4$, taken together complete a moiety selected from the group, $=G$ (oxo or thioxo), $-G-CH_2CH_2-G-$, $-G-CH_2CH_2CH_2-G-$, $-G-CH_2CH(CH_3)CH_2-G-$, $-GCH_2C(CH_3)_2=CH_2G-$, $=N\sim OH$, and $=N\sim OC(=O)CH_3$, wherein each G is oxygen or bivalent sulfur;

X and Y are independently selected from the group consisting of hydrogen, a halogen having an atomic number from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxyacylamino ($-NHC(=O)R_6$ wherein $R_6$ is hydrogen or $C_1$ to $C_2$-alkyl);

p and n are whole number integers selected from the group zero, 2, 3 or 4 such that one of p and n is always zero and the other of p and n is 2, 3 or 4, q is zero or 1;

E is oxygen or bivalent sulfur;

provided that when R is $C_1$ to $C_3$-alkyl, $R_1$ and $R_2$, taken together with the nitrogen to which they are bonded complete a pyrrolidinyl ring, p is 3 and n is 0, q is 1, X and Y are chlorine in the 3 and 4 positions, $R_3$ is not hydroxy, $C_1$ to $C_2$-alkyloxy or $C_1$ to $C_3$-alkanoyloxy;

or a pharmaceutically acceptable salt thereof.

Thus, these compounds are described so that the oxy or thio-group substituent(s) ($R^3$ and $R^4$) are bonded to a cycloaliphatic ring carbon atom which is adjacent to the ring carbon atom bearing the amido-nitrogen or amino-nitrogen of the compounds.

The compounds of Formula I or their acid addition salts in their crystalline state may sometimes be isolated from their reaction mixtures as solvates, i.e., with a discrete quantity of solvent, e.g., water, ethyl acetate, methanol, and the like, associated physically, and thus not affecting the chemical entity per se.

It will be recognized by those in the organic chemical art that the carbon atoms at positions 1 and 2 of the cycloaliphatic ring of structure (I) to which nitrogens are bonded are asymmetrically substituted. Likewise, for certain definitions of $R_3$ and $R_4$, the cycloaliphatic ring carbon atom to which $R_3$ and $R_4$ are bonded may also be asymmetrically substituted. Each of these three carbon atoms can independently possess an R or S—configuration and thus a compound of the formula (I) may have as many as $2^3$ or 8 stereoisomers which comprise four pairs of enantiomers; each enantiomeric pair is termed a racemate. See, for example, J. B. Henderickson, D. J. Cram, and G. S. Hammond, Organic Chemistry, Third Edition, McGraw-Hill Book Company, New York, N.Y., 1970, pages 198–230, particularly pages 207, 208, 213, 215. Of the four racemates, two will have the nitrogen-containing groups at positions 1 and 2 of structure (I) in a trans orientation: that is, the groups will be on opposite sides of the plane of the cycloaliphatic ring; such compounds will be generally referred to in this specification as trans compounds and are meant to include both possible configurations of the third substituted ring carbon if it is asymmetrically substituted. The other two racemates will have the nitrogen-containing groups at positions 1 and 2 of structure (I) in a cis orientation: that is, the groups will be on the same side of the cycloaliphatic ring; such compounds will be generally referred to in this specification as cis compounds and are meant to include both possible configurations of the third substituted ring carbon atom if it is asymmetrically substituted. The four racemates of structure (I) compounds can each exist as a mixture of the two enantiomers or each enantiomer of each pair can be separated by conventional methods. This invention includes within its scope all enantiomeric and diastereomeric forms of the formula I compounds either in pure form or as mixtures of enantiomers or diastereomers. In Charts A through I below, when a particular enantiomer or diastereomer or set of enantiomers or diastereomers is illustrated, the intent is only to convey relative stereochemistry. When it is desired to specify for a formula (I) compound the configuration of the other asymmetric centers relative to that of position 1, this is done according to the Chemical Abstracts Service publication, "Naming and Indexing of Chemical Substances for CHEMICAL ABSTRACTS during the Ninth Collective Period (1972–1976)," a reprint of Section IV (Selection of Index Names for Chemical Substances) from the CHEMICAL ABSTRACTS Volume 76 Index Guide. Accordingly, the relative stereochemistry of three asymmetric carbon atoms in the cycloaliphatic ring of formula I compounds is indicated by: (1) the arbitrary designation of $1\alpha$ for the orientation of the substituent on (asymmetric) carbon atoms number one; (2) the designation $2\alpha$ or $2\beta$ when the substituent on (asymmetric) carbon atom number two is on the same or opposite side of the plane of the cycloaliphatic ring, respectively, relative to said $C_1$ substituent; and (3) the designation $\chi\alpha$ or $\chi\beta$ when the substituent on (asymmetric) carbon atoms number x is on the same or opposite side of the plane of the cycloaliphatic ring, respectively, relative to said $C_1$ substituent.

Two isomers which differ only in the stereochemistry at one asymmetric carbon atom of the cycloaliphatic ring are sometimes herein referred to as epimers.

In the Formula I compounds, the halogens having atomic numbers of from 9 to 35 are fluorine, chlorine and bromine, the term "$C_1$ to $C_3$-alkyl" means methyl, ethyl, n-propyl and isopropyl.

A most preferred subgroup of these formula I compounds are those wherein p is 0, n is 2, 3 or 4, so that the cycloaliphatic ring has 5 to 7 ring carbons, q is 0 or 1, and at least one of X and Y is a halogen having an atomic number of from 9 to 35 in the 3- or 4-positions or both of X and Y are halogens having an atomic number of from 9 to 35, one of X and Y being in the 3-position and the other of X and Y being in the 4-position of the phenyl ring; R is hydrogen or $C_1$ to $C_3$-alkyl; $R_1$ and $R_2$ are taken together with the nitrogen to which they are bonded to complete an azetidinyl, pyrrolidinyl or piperidinyl ring; and E is oxygen; G is oxygen; and the pharmaceutically acceptable salts thereof. Examples of compounds of this group include the cis and trans isomers of:

3,4-difluoro-N-methyl-N-[7-(1-azetidinyl)-1,4-dioxaspiro[4.5]dec-6-yl]benzeneacetamide, 4-bromo-N-[8-(1-piperidinyl)-1,5-dioxaspiro[5.5]undec-7-yl]benzamide, 3,4-dibromo-N-ethyl-N-[8-(1-pyrrolidinyl)-3,3-dimethyl-1,5-dioxaspiro[5.6]dodec-7-yl]benzeneacetamide, 3-bromo-N-(n-propyl)N-[7-(1-pyrrolidinyl)-1,4-dioxaspiro[4.5]dec-6-yl]benzamide, 3,4-dichloro-N-methyl-N-[7-(1-azetidinyl)-1,4-dioxaspiro[4.6]undec-6-yl]benzeneacetamide, 4-bromo-N-[7-(1-pyrrolidinyl)-1,4-dioxaspiro[4.4]non-6-yl]benzamide, 3,4-difluoro-N-[6-methoxy-2-(1-piperidinyl)cyclohexyl]-N-methylbenzamide, and the like, and the pharmacologically acceptable salts thereof.

Another preferred group of compounds of the Formula I type are those wherein p is 0, n is 2, 3 or 4, so that the cycloaliphatic ring has 5 to 7 ring carbons, q is 0 or 1, and at least one of X and Y is a halogen having an atomic number of from 9 to 35 in the 3- or 4-positions or, both of X and Y are halogens having an atomic number of from 9 to 35, one of X and Y being in the 3-position and the other of X and Y being in the 4-position of the phenyl ring, R is hydrogen or $C_1$ to $C^3$-alkyl;, $R_1$ and $R_2$ are each hydrogen or $C_1$ to $C_3$-alkyl; E is oxygen; and G is oxygen; and the pharmaceutically acceptable salts thereof. Examples of such compounds include:

3,4-difluoro-N-[8-(diethylamino)-1,5-dioxaspiro[4.6]undec-7-yl]benzeneacetamide, 4-bromo-N-methyl-N-[[7-(di-n-propyl)amino]1,4-dioxaspiro[5.5]undec-6-yl)benzamide, N-[6-acetyl-2-(dimethylamino)cyclohexyl]-3,4-dichloro-N-(n-propyl)benzeneacetamide, (2-amino-6-propionyloxycyclohexyl)4-fluorobenzamide, and the like, and their pharmacologically acceptable salts.

Another preferred subgroup of formula I compounds are those wherein p is 2, 3 or 4, n is 0, so that the oxy or thio group substituent is on the cycloaliphatic ring carbon atom adjacent the carbon atom bearing the basic amino nitrogen. Examples of such compounds include:

N-ethyl-4-fluoro-N-[2-(1-piperidinyl)-3-(propionyloxy)-cyclohexyl]benzamide, 3,4-dibromo-N-propyl-N-[6-(1-pyrrolidinyl)-1,4-dioxaspiro[4.6]undec-7-yl]benzeneacetamide, 3,4-dichloro-N-[7-(dimethylamino)-1,5-dioxaspiro[5.6-]dodec-8-yl]benzamide, 4-bromo-N-[3-methoxy-2-(1-pyrrolidinyl)cycloheptyl]-N-methylbenzamide, and the pharmacologically acceptable salts thereof.

In general, the new compounds of formula I can be prepared by reacting the selected 1,2-cycloaliphatic diamine of formula II, wherein p, n, R, $R_1$, $R_2$, $R_3$ and $R_4$ are as defined above with a suitable acyl source such as: (1) the appropriate aracyl imidazole of formula III wherein q, E, X and Y are as defined above; (2) an acyl halide of formula IV wherein M is chloride or bromide and q, E, X and Y are as defined above, in the presence of an acid scavenger such as triethylamine; or (3) the carboxylic acid of formula V where q, E, Z and Y are as defined above, in the presence of a condensing agent, in an organic solvent for the reactants, preferably in an ether solvent such as diethyl ether or a cyclic ether solvent such as tetrahydrofuran (THF) or dioxane, or the like, until the compound of the invention is produced. Carbodiimides such as dicyclohexylcarbodiimide or diisopropylcarbodiimide can be used as condensing agents.

The reactants (II) and (III) or (II) and (IV) or (II) and (V) can be mixed in substantially equimolar proportions to effect formation of the desired product (I), but in cases where the non-pertinent amino nitrogens are protected against reaction, if one of the reactants (II), (III), (IV) and (V) is more expensive than the other, it is sometimes preferred to use a stoichiometric excess of the less expensive reactant to insure that substantially all of the more expensive reactant is consumed in the reactions. The reaction will proceed at ambient temperature for most combinations of reactants, but for some combinations of reactants, variations from the initial to final reaction conditions may vary between $-25°$ C. and reflux temperature of the mixture depending on the reactivity of the reactants, the desired reaction time, the solvent being used, the molar proportions, and similar factors of concern to the chemist operating the process. When the new compound of this invention is to be one of formula (I) in which one or both of $R_1$ and $R_2$ are to be hydrogen, the amino-hydrogens in the $R_1$ and/or $R_2$ positions must first be protected by procedures known in the art, then the N-protected diamine reactant (IIa) wherein R, $R_3$, $R_4$, n and p are as defined for formula II and each "—H—Q" denotes that if present, an amino hydrogen has been protected from reaction, is reacted with the selected aracyl imidazole (III) or with the acyl halide (IV) or with the carboxylic acid (V) in the presence of a condensing agent to form the N-[2-(N-protected-amino)oxy or thio-group-substituted cycloaliphatic]-benzamide or -phenylacetamide, which is then treated to remove the N-protecting group to leave as product the desired N-[2-(amino)oxy or thio-group-substituted-cycloaliphatic]benzamide or -phenylacetamide.

Procedures for preparing the aracyl imidazoles (III) and acyl halide (IV) reactants used to form compounds of this invention are known in the art. See, for example, R. B. Wagner and H. D. Zook, SYNTHETIC ORGANIC CHEMISTRY, 1953, John Wiley and Sons, Chapter 17, p. 546 et seq. The aracyl imidazole can be prepared in situ by reacting carbonyldiimidazole with the acid of the formula (V) in an organic solvent. Carboxylic acids of the formula (V) are known in the art or are prepared by known methods.

Acid addition salts can be prepared by reacting a Formula I free base with a stoichiometric amount of an acid, such as hydrogen chloride, hydrogen bromide, hydrogen iodide, sulfuric acid, phosphoric acid, acetic acid, lactic acid, citric acid, succinic acid, benzoic acid, salicyclic acid, pamoic acid, cyclohexanesulfamic acid, methanesulfonic, naphthalenesulfonic, p-toluenesulfonic, maleic, fumaric, oxalic acids and the like. The reaction can be carried out in aqueous or organic liquid solvent, non-aqueous media such as diethyl ether, ethyl acetate, and the like. Non-aqueous media are preferred. When it is desired to obtain optically resolved products in crystalline form it may be more convenient to form salts such as maleates, citrates or pamoates rather than the inorganic acid addition salts, such as the hydrochlorides. Also, whereas oxalic acid and other equivalent acids can be used to produce the aminoamide product in a more easily handled solid form, e.g., in plant manufacturing isolation procedures, it would preferably not be used as a pharmaceutically acceptable salt form of the amino-amide product.

Procedures for preparing the oxy-group substituted diamines (II) useful for preparing the compounds of this invention are summarized by the reaction Charts A through I.

In these Charts R, $R_1$, $R_2$, $R_6$, n, p, q. E, X and Y are as defined above;

A is —$CH_2CH_2$—, —$CH_2CH_2CH_2$—, —$CH_2CH(CH_3)CH_2$—, or —$CH_2C(CH_3)_2CH_2$—;

$R_5$ is $C_1$ to $C_2$-alkyl;

$R_8$ is hydrogen or $C_1$ to $C_3$-alkyl;

$R_9$ is $C_1$ to $C_2$-alkyl;

r is 2, 3 or 4.

The products of these reactions can be isolated and purified by conventional means. In some of the formulas where wavy lines are used, the wavy line bond (∼) between an oxygen atom and a carbon atom of the cycloalkyl ring can indicate either a solid-line bond (—) (up or above the plane of the ring) or a dashed line bond (---) (down or below the plane of the ring), and thus each of these formulas can represent a mixture of the two oxygen-group epimers or one of the other single epimer of unspecified stereochemistry.

In these Charts $R_{10}$ is R or a suitable nitrogen protecting group; $R_{11}$ is $R_1$ or a suitable nitrogen protecting group; $R_{12}$ is $R_2$ or a suitable nitrogen protecting group; $R_7$ is hydrogen or a suitable nitrogen protecting group. Examples of suitable nitrogen protecting groups are:

(1) benzyl ($C_6H_5$—$CH_2$—);
(2) triphenylmethyl(trityl,($C_6H_5$)$_3$C);
(3) para-toluenesulfonyl (p—$CH_3$—$C_6H_4$—$SO_2$—); and
(4) trialkylsilyl, for example, trimethylsilyl (($CH_3$)$_3$Si—) or tertiary butyldimethylsilyl (($CH_3$)$_3$CSi($CH_3$)$_2$—) and the like.

Introduction and removal of such nitrogen protecting groups are well known in the art of organic chemistry: See, for example, (1) J. F. W. McOmie, Advances in Organic Chemistry, Vol. 3, pages 191–281 (1963);
(2) R. A. Boissonas, Advances in Organic Chemistry, Vol. 3, pgs. 159–190 (1963);
(3) "Protective Groups in Organic Chemistry", J. F. W. McOmie, ed., Plenum Press, New York, 1973, pg. 74.

The amines of the formulas, $HNR_{10}R_7$ and $HNR_{11}R_{12}$ are either known in the art or are prepared by standard methods.

Under certain circumstances it is necessary to protect two different nitrogens with different protecting groups such that one such protecting group can be selectively removed while leaving the second protecting group in place. For example, the trityl and benzyl protecting groups can be used in this way, the trityl group being removable in the presence of the benzyl group under acidic conditions.

The requirements for protective groups in Charts A through I are generally well recognized by one skilled in the art of organic chemical synthesis, and the use, when required, of the appropriate protecting group or groups is indicated in these Charts by the use of the symbols $R_{10}$, $R_{11}$, $R_{12}$, and $R_7$; removal of a protecting group is implied when $R_{10}$, $R_{11}$, $R_{12}$ or $R_7$ is replaced in a subsequent formula by R, $R_1$, $R_2$, or H, respectively; N-protected compounds can be deprotected as desired by known methods.

Chart A outlines a preferred general procedure for preparing some cycloaliphatic diamine starting materials via a silyl-protected hydroxy group on a ring carbon atom adjacent to either of the ring carbon atoms which will bear the amido-nitrogen or the amino-nitrogen atoms.

The starting 2-cycloalken-1-ols are well known in the art. The process beings by oxidation of the desired, selected $C_5$ to $C_7$-2-cycloalken-1-ol (XI) with a suitable organic peracid such as m-chloroperbenzoic acid in a suitable organic solvent such as chloroform, preferably with cooling to 0° C. or lower, to produce the epoxy-cycloalkanol (XII), which is produced as a mixture of two epimers, exemplified by the wavy line chemical bond between the hydroxyl group and the cycloalkyl ring. If desired, known procedures can be used to separate the epoxy-cycloalkanol epimer having the epoxide and hydroxyl functions on the same side of the cycloalkaliphatic ring from the epimer having the epoxide and hydroxyl functions on opposite sides of the plane of the cycloaliphatic ring. In our work with this epoxidation-silylation sequence, the epimer (isomer) having the epoxide and hydroxyl on the same side of the cycloaliphatic ring has been observed to be the more abundant epimer in this intermediate product. The epoxy-cycloalkanol (XII) can be used in this process either as a mixture or after separating the epimers to obtain predominantly specific isomer intermediates.

Subjecting the epoxy-cycloalkanol compounds (XII) to suitable silylating conditions such as with tert-butyl-dimethyl-silylchloride, or an equivalent protecting group, in the presence of imidazole in dimethylformamide (DMF) at about 0° C. provides the silyloxy-epoxy-cycloalkane compound (XIII). Alternatively, one can also silylate the starting $C_5$ to $C_7$-2-cycloalken-1-ol, (XI), before epoxidation, as described above; the double bond of this silylated 2-cycloalken-1-ol compound (XIV) can then be epoxidized to produce the silyloxy-epoxy-cycloalkane (XIII) as a mixture of two epoxide epimers. In our work with this silylation-epoxidation sequence, the epimer with the epoxide and the silyl-protected hydroxyl functions on opposite sides of the plane of the cycloaliphatic ring has been observed to be the more abundant of the two product isomers. That is, by reversing the sequence of the reactions, the minor product isomer from the first described epoxidation-silylation sequence becomes the major product of the silylation-epoxidation sequence.

Reaction of the silyloxy-epoxy-cycloalkane (XIII) with a selected amine, $HNR_{11}R_{12}$, which amine can be used in excess to serve as both reactant and reaction medium, optionally in the presence of water, and at elevated temperature to promote reaction, opens the epoxide ring and places the amine on a carbon atom adjacent to the carbon atom bearing the resulting hydroxyl group to give the silyloxy-amino-alcohol compound (XVII). Alternatively, the silylated-epoxy compound can be reacted with the selected amine $HNR_{11}R_{12}$ in the presence of aluminum oxide in a suitable organic solvent such as diethyl ether at room temperature to obtain the silyloxyamino-alcohol (XVII). Reaction of the silyloxy-amino-alcohol (XVII) with methanesulfonyl chloride in the presence of a suitable acid scavenger such as triethylamine in a suitable organic solvent such as methylene chloride or chloroform, preferably with cooling to around 0° C. forms a resulting methanesulfonate ester intermediate. Then treatment of that methanesulfonate ester reaction mixture with an excess of an amine of the formula $HNR_{11}R_7$, optionally in the presence of water, which reaction replaces the methanesulfonyl ester group with an amine group, forms the silyloxy-cycloaliphatic diamine (XVIII).

Alternatively, here, the silyloxy-epoxy-cycloalkane (XIII) is reacted with an amine of the formula, $HNR_{10}R_7$, which may be used in excess to serve as both reactant and reaction medium, optionally in the presence of water at elevated temperatures, e.g., reflux temperature of the mixture, for a time sufficient to form the silyloxy-amino-alcohol (XV). Then, reaction of the silyloxy-amino-alcohol (XV) with methanesulfonyl chloride, as described above, to form the methanesulfonate ester, followed by reaction of that ester intermediate with the desired $HNR_{11}R_{12}$ amine gives a silyloxy-cycloaliphatic-diamine structure (XVI).

Chart B shows a preferred procedure for acylation-O-deprotection of the silyloxy-cycloaliphatic-diamines (XVI) and (XVIII) of Chart A. The hydroxyl group of the resulting hydroxy 2-amino benzamide or benzeneacetamide compounds of this invention can thus be esterified or etherified in preferred methods to produce further compounds of this invention (XXIII) and (XXIV).

The silyloxy-cycloaliphalic-diamines (XVI) and (XVIII) of Chart A can both be represented by the single generalized formula (XXI) of Chart B. The selected silyloxy-cycloaliphatic diamine compound (XXI) is reacted with a suitable acyl source, as indicated above, followed by treatment of the reaction mixture with a mineral acid in a suitable solvent such as ethanol to remove the silyl group to produce the desired-phenylacetamide or -benzamide alcohol (XXII) of this invention.

The adjacently hydroxy substituted 2-amino-cycloaliphatic phenylacetamide or -benzamide (XXII) is then reacted with an appropriate acid chloride, e.g., acetyl chloride or propionyl chloride, or with an acid anhydride or mixed anhydride in the presence of a base such as pyridine, optionally at elevated temperatures to ensure complete reaction, to form the ester compound (XXIII). Reaction of the adjacently hydroxyl substituted 2-amino-cycloaliphatic phenylacetamide or benzamide (XXII) with a suitable base, e.g., sodium hydride, in a suitable organic solvent such as DMF, followed by addition of a $C_1$ to $C_3$-alkyl halide, of the formula $R_5$—Z (wherein $R_5$ denotes $C_1$ to $C_3$-alkyl and Z denotes chlorine, bromine or iodine, to the mixture produces the alkyl ether compound (XXIV).

In a procedure which is not a preferred one for producing ketals of this invention, the hydroxy amino amide (XXII) is oxidized with Jones reagent (chromic acid in sulfuric acid in water) in acetone solvent to produce the corresponding ketone, which is converted to a ketal of this invention by reaction with an appropriate glycol using standard methodology.

Chart C outlines a preferred general procedure for preparing the adjacent ketal group-substituted cycloaliphatic trans diamine starting materials via the selected cycloaliphatic epoxy ketals. The cycloaliphatic trans diamine ketals so obtained, can then be acylated with the desired acyl group, as described above, to form the desired trans-phenylacetamide or -benzamide having a ketal group on a cycloaliphatic ring carbon atom which is adjacent to a ring carbon atom bearing the amido-nitrogen or the amino-nitrogen.

The starting cycloaliphatic epoxy ketals, having the ketal group on the ring carbon atom adjacent to a cycloalkyl ring carbon atom bearing the epoxy function can be prepared by procedures known in the art, such as are described in *Journal of Medicinal Chemistry*, 1977, Vol. 20, No. 7, pp. 930–934, which describes the preparation of the epoxy cyclohexane ketals 7-oxabicyclo(4.1.0)heptan-2-one ethylene ketal, therein, and which reference refers to *Journal of Organic Chemistry*, Vol. 30, No. 7, July 1965, pp. 2109–2120, which describes a generalized procedure for preparing a variety of cycloalkenone ketals, and *Journal of Medicinal Chemistry*, 1972, Vol. 15, No. 2, pp. 171–177, which describes, inter alia, the preparation of an adjacent epoxy cyclopentane ketal, named 6-oxabicyclo[3.1.0]hexan-2-one ethylene ketal. The various ketals of this invention can be prepared by replacing ethylene glycol with 1,3-propylene glycol, 2-methyl-1,3-propylene glycol or 2,2-dimethyl-1,3-propylene glycol in the preparation.

The Chart C process begins by reacting the selected epoxy cycloalkanone ketal (XXXI) with the desired amine $HNR_{11}R_{12}$ as described above to produce the trans-2-amino-cycloalkanol ketal (XXXII), which cycloalkanol ketal is then reacted with methanesulfonyl chloride, as described above, to prepare the sulfonate ester intermediate, which ester is not usually isolated, and which ester is then reacted with an amine of the formula $HNR_{10}R_7$, as described above to produce trans-cycloalkanediamine ketal compound (XXXIII).

Alternatively, reaction of the starting epoxycycloalkane ketal (XXXI) with an amine of the formula ($HNR_{10}R_7$ as described above, produces trans-2-amino-cycloalkanol ketal (XXXIV), which is then reacted with methanesulfonyl chloride by procedures described above to prepare the unisolated sulfonate ester, which is then reacted with the selected amine of the formula, $HNR_{11}R_{12}$, as described above, to produce the trans diamine ketal (XXXV).

The two trans diamine ketals (XXXIII) and (XXXV) can both be represented by the single generalized formula (XXXVI). This trans diamine ketal compound is reacted with the selected acyl source as described above to produce the trans amino-amide ketal (XXXVII).

Optionally, if it is desired to prepare the hydroxy-trans-amino-amide (XXXIX), one can react the trans-amino-amide ketal (XXXVII) with an aqueous mineral acid such as hydrochloric or sulfuric acid to produce the keto-trans-amino-amide (XXXVIII). The keto-trans-amino-amide (XXXVIII) is then reduced with a suitable reducing agent such as sodium borohydride in a suitable solvent such as ethanol at about 0° C. to 30° C. to produce the hydroxy-trans-amino-amide compound (XXXIX) which is obtained in two isomeric forms of which the more abundant is the isomer having the hydroxyl and the adjacent nitrogen group substituents on opposite sides of the plane of the cycloalophatic ring.

Alternatively, reduction of the keto-trans-amino-amide compound (XXXVIII) with potassium tri-sec-butylborohydride (e.g., K-Selectride TM) in a suitable organic solvent such as tetrahydrofuran, preferably at low temperature, e.g., $-10°$ C. to $+10°$ C., produces the hydroxy-trans-amino-amide (XXXIX) wherein the predominate or exclusive isomer form of the compound is one in which the hydroxyl function and the adjacent nitrogen group substituent are on the same side of the plane of the cycloaliphatic ring.

Of course, the hydroxy-trans-amino-amide compounds (XXXIX) can be used as intermediates to prepare the ester or ether compounds as described above in Chart B.

The processes of Chart D are used in a preferred procedure to prepare cis amino amides of this invention wherein p of Formula I is zero. The starting α-chloro ketones of the formula (XLI) are well known in the art. An α-chloro ketone (XLI) is converted to the chloro enamine (XLII) by standard methods, for example, by the reaction with an amine of the formula, $HNR_{10}R_7$, in the presence of anhydrous magnesium sulfate in a suitable solvent such as benzene or toluene. This chloro enamine (XLII) is reacted with the sodium salt of benzyl alcohol in benzyl alcohol solvent, according to D. Cantacuzene, et al., Tetrahedron Letters, pp. 4807–4810 (1971), to give a benzyloxy enamine (XLIII). This enamine (XLIII) is reacted with a chloroformate of the formula, $Cl-CO_2R_9$, or an acid anhydride of the formula, $(R_9O)_2C=O$ in a suitable inert solvent such as tetrahydrofuran to provide an enamine (XLIV). Hydrogenation of this enamine (XLIV) over a platinum catalyst in a suitable solvent such as ethyl acetate yields a mixture of alcohol epimers of a cis amino ester (XLV). Benzylation of the hydroxyl of a formula (XLV) alcohol gives benzyl ether (XLVI), and subsequent Curtius reaction, that is, for example, reaction with hydrazine to form an acyl hydrazide, which is reacted with nitrous acid to produce an acyl azide, which undergoes Curtius rearrangement to afford after acidification with aqueous hydrogen chloride epimeric benzyloxy cis diamines (XLVII). Conversion of a formula (XLVII) diamine to a hydroxy cis amino amide (XLVIII) is then achieved by introducing the desired $R_1$ and $R_2$ groups (if other than hydrogen) by standard alkylation procedures, manipulating the N-protecting groups to allow acylation of the nitrogen on the ring carbon adjacent to the ring carbon bearing the oxygen substituent as indicated in Chart D, and finally deprotecting. Alternatively, with the proper manipulation of protecting groups using methods described above, the hydroxyl function of the hydroxy cis amino amide is esterified or etherified, or the hydroxyl group is oxidized to provide the corresponding ketone which is converted to a desired ketal of this invention by reaction with the appropriate diol according to standard methods.

The processes of Chart E are somewhat analogous to those of Chart D and are used in a preferred procedure to prepare cis amino amides (LVIII) of an α-chloro ketone (LI) is reacted with an amine of the formula, $HNR_{11}R_{12}$, as described for Chart D to provide an enamine (LII). This enamine (LII) is converted to a benzyloxy cis diamine (LVII) (as a mixture of benzyloxy epimers) as described for the analogous transformation in Chart D. A benzyloxy cis diamine (LVII) is converted to a hydroxy cis amino amide (LVIII) by alkylation of the primary nitrogen by standard methods, acylation of the same nitrogen as shown in Chart E and (if necessary) deprotection. The hydroxyl function of a formula (LVIII) hydroxy cis amino amide is reacted to produce desired ester, ether, ketone or ketal compounds of this invention as described above for a formula (XLVIII) compound of Chart D.

The processes of Chart F are used to prepare cis amino amide ketals (LXVII) of this invention wherein p of formula I is zero. As described above, the starting ketal epoxides of the formula (LXI) are known in the art or can be prepared by methods known in the art. A ketal epoxide (LXI) is reacted with an amine of the formula, $HNR_{11}R_{12}$, by a method described above, to afford a trans amino alcohol (LXII). The hydroxyl of an amino alcohol (LXII) is oxidized with Jones reagent, as described above, in acetone to give an amino ketone (LXIII), which is reacted with an amine of the formula, $H_2NR_{10}$, to give an imine (LXIV). Reduction of imine (LXIV) with a suitable reducing agent such as lithium aluminum hydride or sodium cyanoborohydride produces a mixture of cis and trans diamino ketals of the formulas (LXV) and (LXVI), respectively, which mixture can be separated or reacted in the next step. A cis diamino ketal (LXV) (or a cis-trans mixture of diamines (LXV) and (LXVI) from the reduction step) is reacted with a suitable acyl source as described above to provide after purification a cis amino amide ketal (LXVII). A cis amino amide ketal (LXVII) is reacted with mineral acid as described above to generate a cis amino amide ketone, which is reduced to the epimeric alcohols by reduction with a suitable reducing agent as described above. An alcohol thus produced is converted to a cis amino amide ester or ether compound of this invention as described above.

The processes of Chart G are somewhat analogous to those of Chart F and using methods described above are used to prepare cis amino amide ketals (LXXVIII) of this invention wherein n of formula I is zero. A ketal epoxide (LXXI) is reacted with an amine of the formula, $HNR_{10}R_7$, to afford a trans amino alcohol (LXXII), which is oxidized, e.g., with Jones Reagent as defined above, to an amino ketone (LXXIII). An amino ketone (LXXIII) is reacted with an amine of the formula, $H_2NR_8$, to provide an imine (LXXIV), which is reduced to yield a mixture of cis and trans diamino ketals of the formulas (LXXV) and (LXXVI). A cis diamino ketal (LXXV) (or a cis-trans mixture (LXXV) and (LXXVI) from the reduction step) is alkylated by standard methods to introduce the desired $R_{11}$ and $R_{12}$ substituents to afford cis amino ketal (LXXVII), which is reacted with a suitable acyl source as described above to yield after purification a cis amino amide ketal (LXXVIII). A cis amino amide ketal (LXXVIII) is reacted with mineral acid as described above to give a cis amino amide ketone, which is reduced to the epimeric alcohols by reduction with a suitable reducing agent as described above. An alcohol thus produced is converted to a cis amino amide ester or ether compound of this invention as described above.

The processes of Chart H are used to prepare cis amino amide alcohols (LXXXVIII), wherein p of formula I is zero. The starting allylic bromides of the formula (LXXXI) are well known in the art. An allylic bromide (LXXXI) is reacted with an amine of the formula, $HNR_{11}R_{12}$, in the presence of triethylamine, to afford an amino olefin of the formula (LXXXII), which is epoxidized to give after purification an epoxide (LXXXIII). An epoxide (LXXXIII) is reacted with an amine of the formula, $H_2NR_{10}$, to give a diamino alcohol (LXXXIV), which is reacted with chlorosulfonic acid. The resulting sulfate ester is reacted with sodium hydroxide to give an amino aziridine (LXXXV). Alternatively an aziridine (LXXXV) is obtained from the amino olefin (LXXXII) by a method described by F. Fieser and L. Fieser, *Reagents for Organic Synthesis*, Volume 2, Wiley-Interscience, New York, N.Y., 1969, page 223. Reaction of an amino olefin (LXXXII) with iodine isocyanate produces a trans iodo isocyanate which is converted to a carbamate by reaction with methanol. This carbamate is reacted with potassium hydroxide methanol to produce, after purification, an aziridine, which can be alkylated if necessary to give an aziridine of the formula (LXXXV). Heating an aziridine (LXXXV) with a carboxylic acid of the formula, $R_6CO_2H$, gives a diamino ester (LXXXVI). Acylation of a diamino ester (LXXXVI) with a suitable acyl source as described above yields a cis amino amide ester (LXXXVII) of this invention. Saponification of the ester group of a formula (LXXXVII) ester by standard methods affords a cis amino amide alcohol (LXXXVIII) of this invention. Using methods described above, an alcohol (LXXXVIII) is converted to ether compounds of this invention, or such alcohol is oxidized with Jones reagent in acetone to provide a ketone. Using methods described above, this resulting ketone is converted to a desired ketal of this invention or this ketone is reduced to give the alcohol epimer with stereochemistry substantially opposite to that of the formula (LXXXVIII) alcohol. This epimeric alcohol is converted to ether and ester compounds of this invention by methods described above.

The processes of Chart I are somewhat analogous to those of Chart H and are used to prepare cis amino amide alcohols of the formula (XCIX), wherein n of the formula I is zero. An allylic bromide (XCI) is reacted with an amine of the formula, $HNR_{10}R_7$, in the presence of triethylamine, to give an amino olefin (XCII), which is epoxidized to give after purification an epoxide (XCIII). An epoxide (XCIII) is reacted with an amine of the formula, $H_2NR_8$ to give a diamine alcohol (XCIV), which is reacted with chlorosulfuric acid. The resulting sulfate ester is reacted with sodium hydroxide to give an amino aziridine (XCV). Alternatively an amino olefin (XCII) is converted to an aziridine (XCV) by the iodine isocyanate method described above. Heating an aziridine (XCV) with a carboxylic acid of the formula, $R_6CO_2H$, gives a cis diamino ester (XCVI). Alkylation of the nitrogen on a ring carbon atom adjacent to the ring carbon atom bearing the oxygen substituent by standard methods gives a cis diamino ester (XCVII). Acylation of a cis diamino ester (XCVII) with a suitable acyl source as described above yields a cis amino amide ester (XCVIII) of this invention. Saponification of the ester group of a formula (XCVIII) ester by standard methods yields a cis amino amide alcohol (XCIX) of this invention. Using methods described above, an alcohol (XCIX) is converted to ether compounds of this invention or such alcohol is oxidized with Jones reagent in acetone to provide a ketone. Using methods described above, this resulting ketone is converted to a desired ketal of this invention or this ketone is reduced to give the alcohol epimer with stereochemistry substantially opposite to that of the formula (XCIX) alcohol. This epimeric alcohol is converted to ether and ester compounds of this invention by methods described above.

Compounds of this invention of formula (I) wherein $R_3$ and $R_4$ taken together contain sulfur are prepared from dioxaspiro (ketal) compounds of this invention by deketalization as described above to give the corresponding ketone, followed by reaction of this ketone with the appropriate sulfur-containing glycol by known methods, for example, in the presence of boron trifluoride etherate. Ketones described herein can be converted to oximes by known methods, for example, by reaction with hydroxylamine in the presence of sodium hydroxide, making ue of known methods of protection such that substituent groups are not undesirably altered. Such optionally protected oximes are reacted with sodium hydride in a suitable solvent such as dimethylformamide followed by addition of acetyl chloride to the mixture to afford the corresponding acetoxime, making use of known methods of protection if necessary.

The term "dosage unit form" as used in this specification and in the claims refers to physically discrete units suitable as unitary dosages for mammalian subjects, each unit containing as the essential active ingredient a predetermined quantity of a compound of this invention with the required pharmaceutical means which adapt said ingredient for systemic administration. The specification for the novel dosage unit forms of this invention are dictated by and directly dependent on the physical characteristics of the essential active ingredient and the particular effect to be achieved in view of the rlimitations inherent in the art of compounding such an essential active material for beneficial effects in humans and animals as disclosed in detail in this specification under preferred embodiments, those being features of the present invention. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of these amino-amide active ingredients in combination with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, acacia, polyvinylpyrrolidohe, polyvinyl alcohol and the like. In the case of injectable forms, the injectable formulation must be sterile and must be fluid to the extent that easy syringeability exists. Such preparations must be stable under the conditions of manufacture and storage, and ordinarily contain in addition to the principal solvent or suspending liquid, preservatives in the nature of bacteriostatic and fungistatic agents, for example, parabens, chlorobutanol, benzyl alcohol, phenol, thimerosal, and the like. In many cases, it is preferable to include osmotically active agents, for example, sugars or sodium chloride in isotonic concentrations. Carriers and vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.5 to about 350 mg of the essential active ingredient per dosage unit form, which as aforesaid may be in the form of a semi-solid or solid, topical, oral or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain analgesic effects within the aforesaid effective non-toxic range. Expressed otherwise, when used systemically, an amount of the essential active ingredient is provided to a recipient within a range from about 0.01 mg per kg to about 5 mg per kg of body weight of the recipient.

Preferred dosages for most applications are 0.05 to 2.0 mg per kg of body weight.

The useful pharmaceutical dosage unit forms of these compounds in pharmaceutical formulations is preferably adapted for systemic administration to obtain analgesic effects comprising an effective, non-toxic amount of a compound according to Formula I or as its pharmacologically acceptable salt.

Further, the invention relates to methods of obtaining analgesic effects in mammals, for example, humans and valuable warm-blooded animals such as dogs, cats, horses and other commercially valuable animals, by administering systemically to the mammals the aforesaid pharmaceutical dosage unit forms supplying an effective, non-toxic amount for analgesic effects. These preferred compounds have an advantage, to a greater extent, depending upon the particular compound, of having lower physical dependence liability than known analgesic compounds such as morphine and methadone, as shown by evaluation of representative compounds and those standard analgesic drug compounds in various pharmacological test procedures which measure analgesia and the physical dependence liability of the test compounds in standard laboratory test animals.

Representative examples of these Formula I compounds have $ED_{50}$ values of less than about 75 mg/kg s.c. (subcutaneous administration) in standard laboratory animal analgesic tests such as the tail flick, pinch, and hydrochloric acid writhing tests, and the more potent of them have $ED_{50}$ values of less than 10 mg/kg (s.c.) in these tests, while at the same time giving quite high values (greater than 250 mg/kg s.c.) in the naloxone jumping test thus possessing low apparent physical dependence liability as compared to commercial analgesics used as standards. The procedures used to determine these properties of these new compounds were essentially those of Way et al., (Way, E. L. et al., "Simultaneous Quantitative Assessment of Morphine Tolerance and Physical Dependence", *J. Pharmacol. Exp. Ther.*, 167, pp. 1-8 (1969)) and Saalens et al., (Saalens, J. K. et al., The Mouse Jumping Test—A Simple Screening Method to Estimate the Physical Dependence Capacity of Analgesics", *Arch. Int. Pharmacodyn.*, 190, pp. 213-218 (1971)). Statistical effective doses ($ED_{50}$ values) and 95% confidence limits were calculated by the method of Spearman and Karber (Finney, D. J., "Statistical Methods in Biological Assay", Hafner Publ., (1952).

For example, representative preferred compounds of Formula I give low analgesic $ED_{50}$ values (less than about 10 mg of test compound/kg of animal body weight, subcutaneous administration route) in standard laboratory animal tests while at the same time possessing quite high $ED_{50}$ values (greater than 250 mg/kg s.c) in the maxolone jumping test, evidencing substantial freedom from apparent physical dependence liability. In contrast, known analgesic drugs such as morphine and methadone exhibit analgesic $ED_{50}$ values of less than 2 mg/kg s.c., respectively, in these standard analgesic tail flick, pinch and writhing tests, but are known to have high apparent physical dependence liability effects, and this is confirmed by their (morphine and methadone) having relatively low naloxone jumping $ED_{50}$ values ranging from 12 to 30 mg/kg s.c. Other representative compounds of this invention have analgesic potencies somewhat less than the preferred compounds (analgesic activity $ED_{50}$ values up to about 75 mg/kg s.c., in these standard tests), and some such compounds still are characterized by having only low to moderate apparent physical dependence liability.

This invention is further exemplified by the following detailed examples, the procedures of which can be used to prepare compounds of this invention, but these examples are not intended to limit the scope of the invention. All temperatures are in degrees centigrade unless otherwise noted. For brevity, Hg means mercury, bp means boiling point, $CH_2Cl^2$ means methylene chloride solvent, $K_2CO_3$, $MgSO_4$ or $Na_2SO_4$ means the organic layer was dried over anhydrous forms of these salts, mp means melting point, NMR means a nuclear magnetic resonance spectrum, and DBN means 1,5-diazabicyclo[4.3.0]non-5-ene; h means hour(s), $N_2$ means nitrogen, tlc means thin layer chromatography procedures, $Na_2SO_3$ means sodium sulfite, $NaHCO_3$ means sodium bicarbonate, DMSO is dimethylsulfoxide, Skellysolve B (or Skelly B) is a tradename for a solvent of essentially n-hexane, bp 60°-68° C. (Merck Index, Ninth Edition ((1976) page 1106), $Et_2O$ means diethyl ether, MeOH means methaol, THF means tetrahydrofuran, $H_2O$ means water, $CHCl_3$ means chloroform, brine is saturated aqueous sodium chloride solution, DMF means N,N-dimethylformamide, $Et_3N$ is triethylamine, HRMS means high resolution mass spectrum, EtOAc means ethyl acetate, GC (or g.c.) means gas chromatography, GLPC means gas liquid phase chromatography.

EXAMPLE 1

(1α,2β, 3β)-4-Bromo-N-[3-methoxy-2-(1-pyrrolidinylcyclohexyl]-N-methylbenzamide and its monohydrobromide (1α,3β,6α)-2-[[(1,1-dimethylethyl)dimethylsilyl]oxy]-7-oxa-bicyclo[4.1.0]heptane To a stirred solution of 10 g (0.0978 mole) of 2-cyclohexen-1-ol and 20.42 g (0.3 mole) of imidazole in 125 ml DMF was added a solution of 15.07 g (0.1 mole) of t-butyldimethylsilyl chloride in 125 ml DMF at 0° under $N_2$ over a two hour period. The mixture was stirred for two hours at 0° and 30 minutes at ambient temperature. The mixture was diluted with 400 ml $Et_2O$ and washed three times with 325 ml $H_2O$, 250 ml brine, dried ($MgSO_4$) and concentrated in vacuo. The residue was vacuum distilled giving 15.0 g, bp 68°-69° (0.45 mm) (72%) of the silyl ether protected alcohol.

A solution of 15.0 g (0.0706 mole) of the above silyl ether in 200 ml $CHCl_3$ at 0° was treated with 14.05 g (0.0642 mole) of m-chloroperoxybenzoic acid over 15 minutes. The mixture was stirred for three hours at 0° and then placed in the refrigerator overnight. The slurry was filtered and the filtrate washed with 100 ml saturated $Na_2SO_3$, three times with 100 ml saturated $NaHCO_3$, 100 ml $H_2O$, 100 ml brine, dried ($MgSO_4$) and concentrated in vacuo. The residue was distilled at reduced pressure to give 13.0 g (81%) of a 86:15 (1α,2β,6α): (1α,2α,6α), by GLPC) mixture of epoxy ethers.

A 6 g aliquot of this epoxy ether mixture was chromatographed on 325 g silica gel eluting with EtOAc-hexane, 5:95 (v:v) to give 4.5 g of the pure subtitled (1α,2β,6α) isomer. The NMR spectrum was consistent with the named intermediate compound.

B.

(1α,2β,6β)-2-[[(1,1-Dimethylethyl)dimethylsilyl]oxy]6-(1-pyrrolidinyl)cyclohexanol and (1α,2β,6α)-2-[[(1,1-Dimethylethyl)dimethylsilyl]oxy]-6-(1-pyrrolidinyl) cyclohexanol and their hydrobromide salts A mixture of 4.5 g (19.7 mmol) of pure (1α,2β,6α) epoxy silyl ether from Part A above and 50 ml of pyrrolidine was refluxed for sixteen hours at which time G.C. showed no starting material and two products in a ratio of 14:86. The unreacted pyrrolidine was removed at reduced pressure leaving 5.5 g of a light yellow oil.

The crude product was chromatographed on 325 g of silica gel eluting initially with NH$_3$—MeOH—EtOAc, 0.4:3.6:96 (v:v) and finally with NH$_3$—MeOH EtOAc 1:9:90 (v:v) to give 0.6 g of pure substituted (1α,2β,6α) isomer and 3.4 g of the pure subtitled (1α,2β,6β) isomer along with 1.0 g of mixed fractions. For each isomer the nmr spectrum was in accord with the structure.

Analytical samples of the amino alcohol isomers were prepared by treating the free base with ethereal HBr to yield the hydrobromide salts:

(1α,2β,6α) isomer HBr (MeOH—EtOAc): mp, 199°-202°; IR (nujol) 3240, 3080 (OH/NH), 1260, 1250 (Si(CH$_3$)$_2$), 1095, 1080, 1065 (Si—O—C/C—O/C—N); mass spec, m/e 299 (M+), 110 (CH$_2$—CH-CN—N(CH$^2$)$^3$(CH$^2$).

Anal. Calcd. for C$_{16}$H$_{34}$BrNSiO$_2$: C, 50.51; H, 9.01; Br, 21.01; N, 3.68. Found: C, 50.63; H, 9.03; Br, 21.14; N, 3.79 Si(1α,2β,6β) isomer.HBr: mp, 162°-163°. Anal. Found: C, 50.61; H, 8.88; N, 3.94; Br, 20.96

C.
(1α,2α,6β)-1-[2-[[(1,1-Dimethylethyl)dimethylsilyl]oxy]-6-(methylamino)cyclohexyl]pyrrolidine To an ice cold solution of 3.4 g (0.0114 mole) of the (1α,2β,6β) amino alcohol from Part B above and 1.94 g (0.0192 mole) of Et$_3$N in 50 ml CH$_2$Cl$_2$ was added 1.57 g (0.0137 mole) of methanesulfonyl chloride over thirty minutes under N$_2$. A tlc check indicated an incomplete reaction and 0.25 ml of additional methanesulfonyl chloride was added. After one hour, the product was distributed between CH$_2$Cl$_2$ and H$_2$O, the organic phase was separated, dried (MgSO$_4$) and concentrated in vacuo at ambient temperature. The residue was treated with 20 ml of anhydrous methylamine, placed in a stainless steel bomb and heated to 60° for twenty hours. The excess methylamine was evaporated and the residue distributed between EtOAc and H$_2$O. The organic phase was separated, dried (MgSO$_4$) and concentrated in vacuo leaving 3.1 g (86%) of the crude subtitled diamine which was used without further purification.

D.
(1α,2β,3β)-4-Bromo-N-[3-hydroxy-2-(1-pyrrolidinyl)-cyclo-hexyo]-N-methylbenzamide To a stirred solution of 3.04 g (0.0097 mole) of (1α,2α,6β)-1[2[[(1,1-dimethylethyl)dimethylsilyl]oxy]-6-(methylamino)cyclohexyl]pyr-rolidine, from Part C above, and 1.17 g (0.0116 mole) of Et$_3$N in 175 ml Et$_2$- was added a solution of 2.55 g (0.0116 mole) of 4-bromobenzoyl chloride in 75 ml Et$_2$O over 30 minutes. The mixture was stirred for two hours before filtering. The filtrate was washed with H$_2$O, 10% NaOH, H$_2$, brine, dried (MgSO$_4$) and concentrated in vacuo leaving 4.8 g of crude product. The residue was chromatographed on 300 g silica gel eluting with MeOH—NH$_4$OH—EtOAc, 0.9:0.1:99 (v:v) to give 3.9 g (81%) of oil which was used without further characterization.

A stirred solution of 0.99 g (0.002 mole) of oil from above in 10 ml 7.1 N EtOH/HCl was heated to 60° for three days. The tlc of an aliquot indicated very little deprotection and HCl gas was bubbled into the solution for one minute to increase the acidity and the mixture was refluxed for twenty hours. The mixture was concentrated in vacuo and the residue was distributed between 10% NaOH and EtOAc. The organic phase was separated, dried (MgSO$_4$) and concentrated in vacuo leaving 0.7 g of product. The product was dissolved in EtOAc and allowed to crystallize slowly. The resultant solid was recrystallized from EtOAc-Skelly B to give 0.15 g (20%) of the subtitled benzamide: mp 150°-154°. The IR and NMR were consistent with the named compound.

Anal. Calcd. for C$_{18}$H$_{25}$BrN$_2$O$_2$: C, 56.70; H, 6.61; Br, 20.96; N, 7.35. Found: C, 57.00; H, 6.51; Br, 20.56; N, 7.4.

E.
(1α,2β,3β)-4-Bromo-N-[3-methoxy-2-(1-pyrrolidinyl)-cyclo-hexyl]-N-methyl-benzamide monohydrobromide A solution of 0.0624 g (0.0026 mole) of NaH (freed from mineral oil by washing with dry THF) in 10 ml DMF was treated with 0.50 g (0.0013 mole) of the hydroxybenzamide from Part D at ambient temperature under N$_2$. After one hour, 0.37 g (0.0026 mole) of CH$_2$I was added and stirred overnight. The mixture was distributed between 400 ml H$_2$O and Et$_2$O. The aqueous phase was washed twice with Et$_2$O and the combined organic phases were washed with brine, dried (MgSO$_4$) and concentrated in vacuo leaving 0.45 g of oil. The residue was treated with HBr/Et$_2$O and the resultant precipitate recrystallized from MeOH—EtOAc to give 0.25 g and 0.13 g (61%) of the titled compound: mp 214°-216°. The IR, NMR and mass spectral analyses were consistent with the named compound.

Anal. Calcd. for C$_{19}$H$_{28}$Br$_2$N$_2$O$_2$: C, 47.91; H, 5.93; Br, 33.56; N, 5.88. Found: C, 47.84; H, 6.08; Br, 33.33; N, 5.95.

EXAMPLE 2

(1α,2β,3α)-4-Bromo-N-[3-methoxy-2-(1-pyrrolidinyl) cyclohexyl]-N-methylbenzamide and its monohydrobromide

A.
(1α,2α,6α)-2-[[(1,1-dimethylethyl)dimethylsilyl]oxy]-7-oxa-bicyclo[4.1.0]heptane.

To a solution of 22.4 g (0.196 mol) of (1α,2α,6α)-2-hydroxy-7-oxabicyclo-[4.1.0]heptane and 41.15 g (0.6 mol) of imidazole in 250 ml of DMF cooled to 0° in an ice-water bath was added dropwise over a two hour period a solution of 30.37 g (0.2 mol) of t-butyl(-dimethyl) chlorosilane in 250 ml of DMF. After the addition was complete the reaction mixture was stirred at 0° for 2.5 hours and then allowed to warm slowly to ambient temperature. The reaction mixture was diluted with 800 ml of Et$_2$O, washed with three 650 ml portions of H$_2$O, brine, dried (MgSO$_4$) and the solvent removed in vacuo leaving 44 g of crude product. The crude product thus obtained was distilled at reduced pressure to give 34.4 g (77%) of the above-named intermediate: bp 65°-67° (0.05 mm); G.C. analysis shows 96% (1α,-2α,6α) isomer and 4% (1α,2β,6α) isomer. The IR and NMR spectral analyses were consistent with the named product.

Analysis Calcd. for C$_{12}$H$_{24}$SiO$_2$: C, 63.10; H, 10.59. Found: C, 63.30; H, 10.90.

B.
(1α,1α,6β)-2-[[(1,1-Dimethylethyl)dimethylsilyl]oxy]-6-(1-pyrrolidinyl)cyclohexanol, monohydrobromide A mixture of 5.0 g (22.0 mmol) of the epoxide product from Part A above, 10 ml of pyrrolidine and 1 ml of H$_2$O was heated at 80° C. for six hours. The bulk of the residual pyrrolidine was removed in vacuo and the residue was diluted with 100 ml of Et$_2$O. The etheral solution was washed with H₂O, brine, dried (MgSO₄) and the solvent removed in vacuo leaving 6.0 g of a light orange oil.

The crude oil product thus obtained was chromatographed on an EM Reagents Lobar size C silica gel column, eluting with MeOH:NH₄OH:THF (0.75:0.50:98.75) to give 1.1 g (16.7%) isomer A ((1α,2β,6β) isomer followed by 3.3 g (50%) of Isomer B, the named (1α,2α,6∞) intermediate.

Isomer A was treated with etheral HBr and the resultant precipitate collected and recrystallized from EtOH/Et₂O: mp 130°–133° (dec). The IR, NMR and mass spectral analyses were consistent with the (1α,2β,6β) epimer of the subtitled intermediate.

An aliquot of Isomer B was treated with etheral HBr and the resultant precipitate collected and recrystallized from EtOH/Et₂O to give the named (1α,2α,6β) intermediate, mp 154°–156°. The NMR and mass spectral analyses were consistent with the named isomer.

Anal. Calcd. for $C_{16}H_{34}BrNO_2Si$: C, 50.51; H, 9.01; N, 3.68; Br, 21.0. Found: C, 50.60; H, 8.89; N, 3.53; Br, 20.87Si.

C.
(1α,2β,6β)-1-[2-[[(1,1-Dimethylethyl)dimethylsilyl]oxy]-6-(methylamino)cyclohexyl]-pyrrolidine, dihydrobromide In an oven dried 3-neck round bottom flask fitted with a dewar condenser, positive N₂ inlet, serum cup and magnetic stir bar was placed a solution of 5.8 g (19.3 mmol) of the (1α,2α,6β) alcohol isomer (free base) from Part B above and 2.2 g (20.4 mmol) of Et₃N in 100 ml of CH₂Cl₂. The reaction mixture was cooled to 0° in an ice-water bath and 2.3 g (20.4 mmol) of methanesulfonyl chloride was added dropwise via syringe over a 10 minute period. The reaction mixture was stirred at 0° for 1.5 hours and the solvent was removed in vacuo. The dewar condenser was then charged with dry ice-acetone and ca. 30 ml of anhydrous methylamine was condensed into the reaction vessel. The resultant solution was rapidly transferred to a glass bomb which was sealed under N₂ pressure. The bomb was heated at 60° for 48 hours and allowed to sit at room temperature for an additional 48 hours.

The bomb was cooled to 0° in an ice-water bath and carefully opened. The excess methylamine was allowed to evaporate in a N₂ stream. The residue was distributed between CH₂Cl₂ and H₂O. The phases were separated, the aqueous phase extracted with CH₂Cl₂, the combined organic phases were washed with brine, dried (MgSO₄) and the solvent removed in vacuo leaving 6.3 g of crude product, the subtitled diamine.

The crude diamine product thus obtained was chromatographed on 275 g of RP-2 silica gel eluting with MeOH—NH₄OH—CHCl₃, 1.0:0.5:98.5 (v:v) to give 3.0 g of the desired product. Rechromatography of mixed fraction on 275 g of RP-2 silica gel eluting with MeOH—NH₄OH—CHCl₃, 0.5:0.5:99 (v:v), gave an additional 1.0 g, total yield 4.0 g (67%) of a water white oil. The NMR spectral analysis was consistent with the named product.

An analytical sample was prepared by treating an aliquot of the chromatographed product with ethereal HBr, collecting the resultant precipitate, and recrystallization from Et₂O: mp 228°–230°. The IR and mass spectral analyses were consistent with the dihydrobromide salt of the named compound.

Anal. Calcd. for $C_{17}H_{38}Br_2N_2OSi$: C, 43.04; H, 8.07; Br, 33.69; N, 5.90. Found: C, 43.25; H, 8.47; Br, 32.99; N, 5.96.

D.
(1α,2β,3α)-4-Bromo-N-[3-[[(1,1-dimethylethyl)dimethylsilyl]-oxy]-2-(1-pyrrolidinyl)cyclohexyl]-N-methylbenzamide To a stirred solution of 4.1 g (13.1 mmol) of the methylamine product from Part C above and 1.59 g (15.7 mmol) of Et₃N in 80 ml of Et₂O was added dropwise over a 20 minute period a solution of 3.45 g (15.7 mmol) of 4-bromobenzoyl chloride in 20 ml of Et₂O. The reaction mixture was stirred at ambient temperature for three hours and filtered. The filtrate was concentrated in vacuo, and the residue dissolved in CH₂Cl₂. The CH₂Cl₂ solution was washed with H₂O, 10% NaOH, brine, dried (MgSO₄) and concentrated in vacuo to give 6.24 g (95%) of the subtitled silylated benzamide which was used in the next reaction without further purification.

An analytical sample was prepared by crystallization from EtOAc-Skelly B to give the pure subtitled silylated benzamide: mp 124°–127° C. The IR and NMR spectral analyses were consistent with the named intermediate.

Anal. Calcd. for $C_{24}H_{39}BrN_3SiO_2$: C, 58.16; H, 7.93; Br, 16.13; N, 5.65. Found: C, 58.19; H, 8.10; Br, 15.76; N, 5.42.

E.
(1α,2β,3α)-4-Bromo-N-[3-hydroxy-2-(1-pyrrolidinyl)-cyclo-hexyl]-N-methyl-benzamide A solution of 3.0 g (6.1 mmole) of the silylated benzamide from Part D above in 75 ml of ca. 7 N ethanolic HCl was heated at 50° for one hour under N₂. The mixture was concentrated in vacuo and the residue distributed between CH₂Cl₂ and 10% NaOH. The organic phase was separated, washed with H₂O, dried (MgSO₄) and concentrated in vacuo. The residue was chromatographed on silica gel eluting with MeOH—EtOAc 2:98 (v:v). The product thus isolated was crystallized from MeOH—Et₂O to give 0.64 g (28%) of the subtitled hydroxy benzamide: mp 120°–125°. The IR and NMR spectral analyses were consistent with the subtitled compound, a compound of this invention.

Analysis Calcd. for $C_{18}H_{25}BrN_2O$: C, 56.70; H, 6.61; Br, 20.96; N, 7.35. Found: C, 56.98; H, 6.90; Br, 20.78; N, 7.14.

F.
(1α,2β,3α)-4-Bromo-N-[3-methoxy-2-(1-pyrrolidinyl)-cyclo-hexyl]-N-methylbenzamide monohydrobromide A slurry of 0.27 g (1.56 mmol) of NaH (50% in oil) in dry THF (freshly distilled from LAH) was decanted twice to remove the mineral oil. The NaH was mixed with 20 ml of DMF and 1.5 g (2.8 mmol) of the hydroxy benzamide from Part E above under N₂. After stirring for one hour at ambient temperature 0.79 g (5.6 mmol) of methyl iodide was added and the reaction stirred for eighteen hours at ambient temperature. The reaction mixture was poured into 400 ml of H₂O and extracted twice with Et₂O. The ethereal extract was combined, washed with H₂O, brine, dried (MgSO₄) and concentrated in vacuo. The oil was treated with Et₂O/HBr and the resultant precipitate recrystallized from MeOH-EtOAc to give 1.0 g (77%) of the named methoxy ether benzamide salt. The analytical sample had: mp 240°–245°. The IR and NMR were consistent with the named compound.

Anal. Calcd. for $C_{19}H_{28}Br_2N_2O_2$: C, 47.91; H, 5.93; Br, 33.56; N, 5.88. Found: C, 47.72; H, 5.96; Br, 33.23; N, 5.71.

EXAMPLE 3

3,4-Dichloro-N-methyl-N-[7-(1-pyrrolidinyl)-1,4-dioxaspiro-[4.5]dec-6-yl]benzeneacetamide, and its monohydrochloride

A. Trans (∓)-1-[6-[methyl(phenylmethyl)amino]-1,4-dioxaspiro-[4.5]dec-7-yl]pyrrolidine monohydrochloride A mixture of 40.6 g (0.26 mole) of spiro[1,3-dioxolane]-2,2'-[7-oxabicyclo[4.1.0]heptane], also named 7-oxabicyclo-[4.1.0]-heptan-2-one-ethylene ketal[1], 32.7 g (0.25 mole) of methyl(phenylmethyl)amine and 35 ml of water was heated on a steambath with stirring for 1.5 hour. The reaction mixture was allowed to stir at ambient temperature overnight. The mixture was then treated with an additional 500 ml of water and steam distilled until the distillate was clear. The residue was distributed between methylene chloride and water. The liquid phases were separated and the aqueous phase was extracted with methylene chloride. The combined organic phases were dried over magnesium sulfate and concentrated in vacuo leaving 71.6 g (100% yield) of crude trans-(∓)-6-hydroxy-N-methyl-N-(phenylmethyl)-1,4-dioxaspiro[4.5]decan-7-amine intermediate.

[1] The above ethylene ketal starting material was prepared as described by R. Vince et al. in "Synthesis . . . Synthesis" in *J. of Med. Chem.*, 20, No. 7 (1977), pg. 930–932.

A solution of 22.19 g (0.08 mole) of the above crude trans-amino alcohol and 15.6 ml (0.112 mole) of triethylamine in 400 ml of methylene chloride was stirred under nitrogen in an ice bath while 11.4 g (0.1 mole) of methanesulfonyl chloride in 25 ml of methylene chloride was added slowly over thirty minutes. The mixture was stirred an additional two hours and the resulting product was distributed between water and methylene chloride. The phases were separated and the aqueous phase was extracted with methylene chloride. The combined organic phases were dried (magnesium sulfate) and concentrated in vacuo at ambient temperature leaving crude mesylate intermediate.

The crude mesylate was cooled in an ice bath while 150 ml of pyrrolidine was added[2]. After ten minutes the bath was removed and the solution allowed to warm to ambient temperature and then heated at 100° for four days. The solution was concentrated in vacuo and the residue distributed between diethyl ether and water. The liquid phases were separated and the aqueous phase extracted with diethyl ether. The combined organic phases were washed twice with water and brine, dried over magnesium sulfate and concentrated under vacuum leaving 29 g (110 percent yield) of crude titled product.

[2] The mesylate is cooled while pyrrolidine is added to avoid the vigorous exotherm which was observed in earlier experiments.

This crude product was chromatographed in 1500 g of silica gel, eluting with a methanol/ammonia/ethylacetate mixture 0.9:0.1:99 (v/v), which was gradually increased to 5.4:0.6:94 (v/v) to give 11.2 g of the desired named product. A mixed fraction of 7.7 g gave a total yield of 18.9 g (71%).

The monohydrochloride salt of this named aminoamide product, obtained from an earlier run was submitted for analysis: m.p. 183°–185° C. The IR and mass spectra analyses were consistent with the named product. The elemental analysis was as follows: Anal. Calcd. for $C_{20}H_{31}ClN_2O_2$: C, 65.47; H, 8.52; Cl, 9.66; N, 7.69. Found: C, 65.29; H, 8.66; Cl, 9.78; N, 7.70.

B. Trans(∓)-1-[6-(methylamino)-1,4-dioxaspio[4.5]dec-7-yl]-pyrrolidine

A solution of 11.2 g (0.034 mole) of the pyrrolidine derivative from Part A above in 250 ml of absolute ethanol was mixed with 11 g of palladium on carbon catalyst in a Parr bottle and placed in a Pan shaker under 50 psi of hydrogen for one hour. The resulting hydrogenated material was filtered through a filter pad (Celite[4]) and the filtrate was concentrated in vacuo leaving 7.0 g (87.5% yield) of crude trans(∓)-1-[6-(methylamino)-1,4-dioxaspiro[4.5]dec-7-yl]pyrrolidine. The NMR spectrum of this material was consistent with the named material.

C. Trans(∓)-3,4-dichloro-N-methyl-N-[7-(1-pyrrolidinyl)-1,4-dioxaspiro[4.5]dec-6-yl]benzeneacetamide, and its monohydrochloride To a stirred solution of 2.4 g (0.01 mole) of trans(∓)-1[6-(methylamino)-1,4-dioxaspiro[4.5]dec-7-yl]pyrrolidine and 1.2 g (0.012 mole) of triethylamine in 150 ml of diethyl ether was added a solution of 2.68 g (0.012 mole) of 3,4-dichlorophenylacetyl chloride in 100 ml of diethyl ether over thirty minutes under nitrogen. The mixture was stirred for two hours at ambient temperature. The slurry was filtered and the filtrate was washed with water, 10 percent sodium hydroxide solution, water and brine and then dried over magnesium sulfate, and concentrated under vacuum, leaving 4.5 g of crude product. The residue was treated with hydrogen chloride in diethyl ether and the resultant precipitate was recrystallized from methanol/ethyl acetate to give 2.5 g (46% yield) of the named final product as its hydrochloride salt, mp 228°–231° C. The IR and NMR spectra were consistent with the named product. The elemental analyses was as follows:

Anal. Calcd. for $C_{21}H_{29}Cl_3N_2O_3$: C, 54.38; H, 6.30; Cl, 22.93; N, 6.04. Found: C, 54.32; H, 6.47; Cl, 22.82; N, 6.29.

EXAMPLE 4

Trans(∓)-3,4-Dichloro-N-[7-(dimethylamino)-1,4-dioxaspiro[4.5]dec-6-yl]-N-methylbenzeneacetamide and its monohydrochloride

A. Trans(∓)-$N^6$-(phenylmethyl)-$N^6,N^7,N^7$-trimethyl-1,4-dioxaspiro[4.5]decane-6,7-diamine A solution of 27.7 g (0.1 mole) of trans-(∓)-6-hydroxy-N-methyl-N-(phenylmethyl)-1,4-dioxaspiro[4.5]decan-7-amine (prepared as described in Example 3A above) in 700 ml of methylene chloride and 14.2 g (0.14 mole) of triethylamine was cooled in an ice bath under nitrogen. A solution of 14.3 g (0.125 mole) of methanesulfonyl chloride in 50 ml of methylene chloride was added slowly over thirty minutes. After thirty minutes the mixture was treated with water, separated, and the organic phase dried (MgSO$_4$) and concentrated in vacuo. The resulting oil was cooled and 100 ml of 40% aqueous dimethylamine was added and after thirty minutes heated to 60° C. for eighteen hours. The temperature was then raised to 100° C. for two days. There was still some mesylate remaining and 50 ml of aqueous methylamine was added and the mixture heated for an additional thirty-six hours. The mixture was diluted with water and extracted with ethyl acetate. The aqueous layer was washed with ethyl acetate and the combined organic phases washed with water, dried (MgSO$_4$) and concentrated in vacuo. The resulting crude oil was vacuum distilled to give 23.2 g, bp 125°–135° C. (0.005 mm). The oil intermediate product was further purified by chromatography on 400 g silica gel eluting with 1 l ethyl acetate:Skellysolve ® B 20:80 (v/v), followed by 1 l ethyl acetate-Skellysolve ® B 40:60 (v/v), 1 l ethyl acetate:Skellysolve ® B 60:40 (v/v), 1 l ethyl acetate and 1 l methanol/ethyl acetate 20:80 (v/v). The following fractions were obtained and their purity determined by gas chromatography: 3.3 g (91%), 14.0 g (75%), 2.0 g (94%), and 1.2 g (97%) (overall yield 67% of the subtitled diamine).

B.
Trans-($\mp$)-N$^6$,N$^7$,N$^7$-trimethyl-1,4-dioxaspiro[4.5]decane-6,7-diamine A solution of 6.5 g (0.0214 mole) of trans-($\mp$)-N$^6$-(phenylmethyl)-N$^6$,N$^7$,N$^7$-trimethyl-1,4-dioxaspiro[4.5]decane-6,7-diamine from Part A above and 6.5 g 10% palladium on carbon catalyst in 250 ml absolute ethanol was placed in a Parr shaker under 50 psi of hydrogen. After thirty minutes the slurry was filtered and the filtrate concentrated in vacuo. The residue was treated with 50% NaOH solution and ethyl acetate, separated, dried (MgSO$_4$) and concentrated in vacuo to give 3 g of crude trans-($\mp$)N-dimethyl-N-[6-(methylamino)-1,4-dioxa-spiro[4.5]dec-7-yl]amine (66% yield).

C. Final Product (named above)

A solution of 1.5 g (0.007 mole) of trans-($\mp$)-N$^6$,N$^7$,N$^7$-trimethyl-1,4-dioxaspiro[4.5]decane-6,7-diamine (Part B above) and 0.78 g (0.0077 mole) of triethylamine in 75 ml diethyl ether was stirred under nitrogen while a solution of 1.72 g (0.0077 mole) of 3,4-dichlorophenylacetyl chloride in 25 ml diethyl ether was added over 0.5 hour to form the named product. After two hours the resulting slurry was filtered and the filtrate washed with H$_2$O, 10% NaOH, H$_2$O, brine, dried (MgSO$_4$) and concentrated in vacuo. The oil was dissolved in ethyl acetate and treated with an ethanol-hydrogen chloride solution and the resulting solid salt was recrystallized twice from a methanol/ethyl acetate mixture to give 1.3 g, mp 233.5–235.5 and 0.52 g, mp 230–233 of the titled amine-amide salt (60% yield). The elemental analysis was as follows:

Anal. Calcd. for C$_{19}$H$_{27}$Cl$_3$N$_2$O$_3$: C, 52.13; H, 6.22; Cl, 24.30; N, 6.40. Found: C, 52.13; H, 6.43; Cl, 24.13; N, 6.33.

EXAMPLE 5

Trans-($\mp$)-4-Bromo-N-[7-(N,N-dimethylamino)-1,4-dioxaspiro[4.5]dec-6-yl]-N-methylbenzamide and its monohydrobromide, methanol solvate A solution of 1.5 g (0.007 mole) of trans-($\mp$)-N$^6$,N$^7$,N$^7$-trimethyl-1,4-dioxaspiro[4.5]decane-6,7-diamine (prepared as in Example 4B above) and 0.78 g (0.0077 mole) of triethylamine in 75 ml of diethyl ether was stirred under nitrogen while a solution of 1.69 g (0.0077 mole) of 4-bromobenzoyl chloride in 25 ml of diethyl ether was added slowly. After two hours, the resulting slurry was filtered and the filtrate was washed with water, 10 percent sodium hydroxide solution, water and brine, dried with magnesium sulfate and concentrated in vacuo. The resulting titled crude aminoamide residue was dissolved in ethyl acetate, filtered to remove an insolubable material, and then treated with diethyl ether/hydrogen bromide mixture. The resulting solid hydrobromide salt was recrystallized twice from a methanol/ethyl acetate mixture to give 2.05 g, mp 156°–160° C., with foaming (61 percent yield). The analysis was as follows:

Anal. Calcd. for C$_{18}$H$_{26}$Br$_2$N$_2$O$_3$-methanol solvate: C, 44.72; H, 5.93; Br, 31.32; N, 5.49. Found: C, 44.82; H, 6.05; Br, 31.07; N, 5.41 ethyl.acetate 1.14%; methanol 7.36%.

EXAMPLE 6

Trans-($\mp$)-4-Bromo-N-methyl-N-[7-(1-pyrrolidinyl)-1,4-dioxaspiro[4.5]dec-6-yl]benzamide and its monohydrobromide To a stirred solution of 1.3 g (0.0054 mole) of trans-($\mp$)1-[6-(methylamino)-1,4-dioxaspiro[4.5]dec-7-yl]pyrrolidine (prepared as in Example 3B above) and 0.657 g (0.0065 mole) of Et$_3$N in 75 ml of diethyl ether was added a solution of 1.43 g (0.0065 mole) of 4-bromobenzoyl bromide in 25 ml of diethyl ether over thirty minutes under nitrogen. The mixture was stirred for two hours at ambient temperature. The slurry was filtered and the filtrate washed with water, 10% NaOH, water, brine, dried (MgSO$_4$) and concentrated in vacuo. The residue thus obtained was treated with diethylether/hydrogen bromide to give 1.57 g (58%) of the subtitled amino-amide, mp 213–216. The IR and mass spectra were consistent with the assigned structure.

Anal. Calcd. for C$_{20}$H$_{28}$Br$_2$N$_2$O$_3$: C, 47.64; H, 5.60; Br, 31.69; N, 5.56. Found: C, 47.38; H, 5.72; Br, 31.32; N, 5.54.

EXAMPLE 7

(1α,2β,6β)-4-Bromo-N-[2-hydroxy-6-(1-pyrrolidinyl)-cyclohexyl]-N-methylbenzamide To 5 ml of concentrated sulfuric acid, cooled in a dry ice acetone bath (H$_2$SO$_4$ forms a slurry at these temperatures) there was added 1.5 g (30 mmole) of trans-($\mp$)-4-bromo-N-methyl-N-[7-(1-pyrrol-idinyl) 1,4-dioxaspiro[4.5]dec-6-yl]benzamide monohydrobromide (prepared as described in Example 6 above). The resulting slurry mixture was allowed to warm slowly until all of the solids had dissolved. The mixture was immediately neutralized by the addition of solid sodium bicarbonate and a small amount of water, while externally cooling the mixture. The resulting basic solution was extracted with methylene chloride and the resulting organic liquid phase was washed with brine solution, dried using magnesium sulfate, and the solvent was removed in vacuo to leave as residue the crude ketone, 4-bromo-N-methyl-N-[2-oxo-6-(1-pyrrolidinyl)cyclohexyl]benzamide.

The crude ketone oil was immediately dissolved in 50 ml of absolute ethanol to which was added 0.23 g (6.0 mmoles) of sodium borohydride. After stirring the mixture at room temperature for one hour, 200 ml of water was added. The mixture was extracted with diethyl ether, the liquid phases were separated, the aqueous phase was saturated with sodium chloride and then extracted with diethyl ether. The combined ethereal phases were washed with brine, dried with magnesium sulfate, and the solvent was removed in vacuo, leaving 1.2 g of curde solid. Three recrystallizations from methanol/ethyl acetate gave 0.55 g (56 percent) of the titled hydroxycyclohexyl compound, mp 149°-155° C.

Anal. Calcd. for $C_{18}H_{25}BrN_2O_2$: C, 59.70; H, 6.61; N, 7.35; Br, 20.96. Found: C, 59.-8; H, 6.62; N, 7.29; Br, 21.15.

EXAMPLE 8 trans-($\mp$)-4-Bromo-N-methyl-N-[6-(1-pyrrolidinyl)-1,4-dioxaspiro[4.5]dec-7-yl]benzamide monohydrochloride

A.

trans-($\mp$)-1-[8-(methylamino)-1,4-dioxaspiro[4,5]dec-6-yl]-pyrrolidine, monohydrochloride A solution of 38.9 g (0.249 mole) of spiro[1,3-dioxalene]-2,2'-[7[oxabicyclo[5.1.0]heptane][1] in 50 ml pyrrolidine and 2 ml $H_2$) was heated to 86° for eighteen hours. The excess pyrrolidine was removed via rotovap and the residue distributed between EtOAc and $H_2O$. The phases were separated and the organic phase washed with $H_2O$, dried ($MgSO_4$) and concentrated in vacuo leaving 31 g of crude oil. The oil was chromatographed on 1500 g of RP-2 silica gel eluting with EtOAc to give 26.5 g (47%) of the trans amino alcohol, trans-($\mp$)-7-(1-pyrrolidinyl)-1,4-dioxaspiro[4.5]decan-6-ol.

[1] The starting material (also named in Example 4A above) was prepared according to the procedure by R. Vince et al. *J.Med.Chem.*, 20, 930 (1977).

A solution of 26.5 g (0.117 mole) of the trans amino alcohol in 3-0 ml $CH_2Cl_2$ and 17.76 g (0.175 mole) of $Et_3N$ was cooled in an ice bath under $N_2$. To this solution was added over a thirty minute period 20.1 g (0.175 mole) of methanesulfonyl chloride and the reaction was stirred for two hours. The mixture was distributed between $CH_2Cl_2$ and $H_2O$, the phases separated, the organic phase dried ($MgSO_4$) and concentrated in vacuo. The residue was placed in a stainless steel bomb with 200 ml of methylamine and heated on a steam bath for two days. The bomb was cooled, vented and the excess methylamine evaporated. The residue was distributed between EtOAc and $H_2O$ and the organic phase separated, washed with $H_2O$, brine, dried ($MgSO_4$) and concentrated in vacuo. The crude oil was chromatographed on 500 g of RP-2 silica gel eluting with EtOAc then MeOH—$NH_4OH$—EtOAc, 1.8:0.2:98 (v:v) to give 14.65 g (50% from the amino alcohol) of the subtitled trans diamine. NMR ($CDCl_3$): δ 0.8–1.9 (m, 10H, ring $CH_2$—), 1.9–2.3 (m, 1H, CH—NH), 2.45 (s, 3H, $CH_3$—N), 2.5–3.2 (m, 5H, $CH_2$—N), 3.75–4.2 (m, 4H, $CH_2O$).

B.

trans-($\mp$)-4-Bromo-N-methyl-N-[6-(1-pyrrolidinyl)-1,4-dioxaspiro[4.5]dec-7-yl]benzamide, monohydrochloride To a stirred solution of 7.2 g (0.03 mole) of trans-($\mp$)-1-[7-(methylamino)-1,4-dioxaspiro[4.5]dex-6-yl]pyrrolidine in 200 ml $Et_2O$ and 3.64 g (0.036 mole) of triethylamine was added a solution of 7.9 g (0.036 mole) of 4-bromobenzoyl chloride in 50 ml $Et_2O$ over thirty minutes under $N_2$. After two hours the slurry was filtered and the salt washed with $Et_2O$. The combined ethereal layers were washed with $H_2O$, 10% NaOH, $H_2O$, brine, dried ($MgSO_4$) and concentrated in vacuo. The residue was treated with $Et_2O$/HCl and the resultant precipitate recrystallized from MeOH EtOAc to give 7.0 g, mp 218°-219° and 1.68 g, mp 212°-214° (56%) of the titled amide: mp 219°-220.5°. The nmr and ir spectra were in accord with the titled amino amide ketal.

Anal. Calcd. for $C_{20}H_{28}BrClN_2O_3$: C, 52.24; H, 6.14; Br 17.38; Cl, 7.71; N, 6. Found: C, 51.88; H, 6.24; Br, 17.36; Cl, 7.78; N, 6.40.

EXAMPLE 9 trans-($\mp$)-4-Bromo-N-methyl-N-[3-oxo-2-(1-pyrrolidinyl)cyclohexyl]benzamide, monohydrobromide To 12 ml of concentrated $H_2SO_4$ in a glass beaker was added 2.2 g (0.0048) of the amino amide ketal prepared as described in Example 8B. The mixture was stirred until the solid had dissolved and the foaming had ceased. The solution was quickly diluted with ice and made basic (pH 14) with 50% NaOH while maintaining ice bath temperatures. The product was extracted with EtOAc and the extract washed with $H_2O$, dried ($MgSO_4$) and concentrated in vacuo. Although the free base was a crystalline compound (mp 145–149), it was unstable as indicated by the broadening of the melting point upon subsequent recrystallizations. Therefore, the hydrobromide salt was made with $Et_2O$/$HB_2$ and the resultant precipitate recrystallized from MeOH—EtOAc to give 0.29 g (16%) of the titled compound: mp 190°-196° C. The ir and nmr spectra were in accord with the titled compound.

Anal. Calcd. for $C_{18}H_{24}Br_2N_2O_2$: C, 46.98; H, 5.26; Br, 34.73; N, 6.09. Found: C, 47.08; H, 5.27; Br, 34.20; N, 5.99.

GENERAL CHEMICAL STRUCTURES

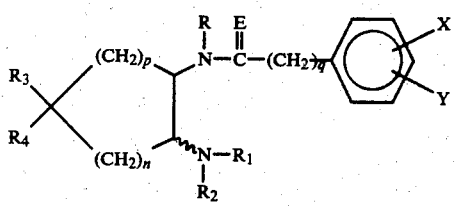

I

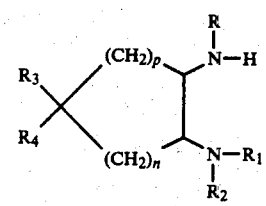

II

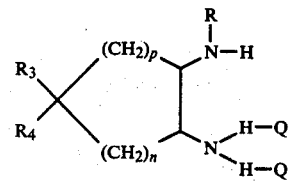

IIa

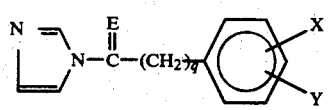

III

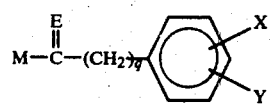

IV

-continued
GENERAL CHEMICAL STRUCTURES
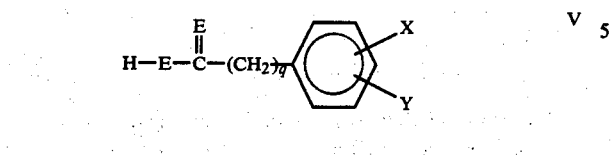
CHART A
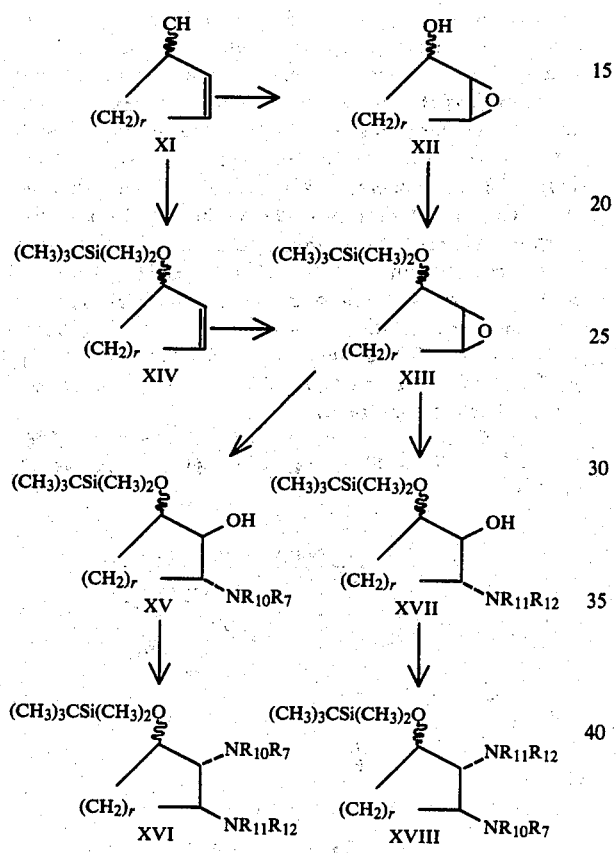
CHART B
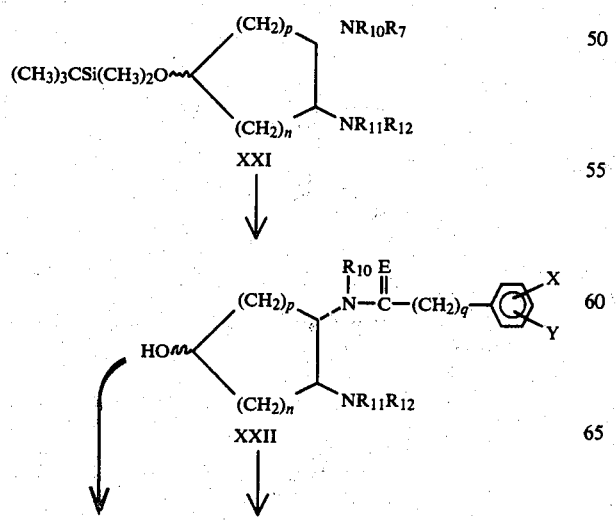
-continued
CHART B
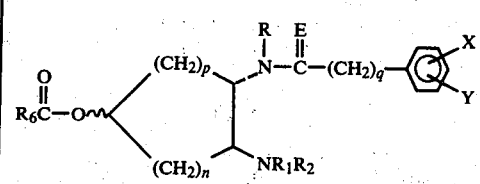
CHART C
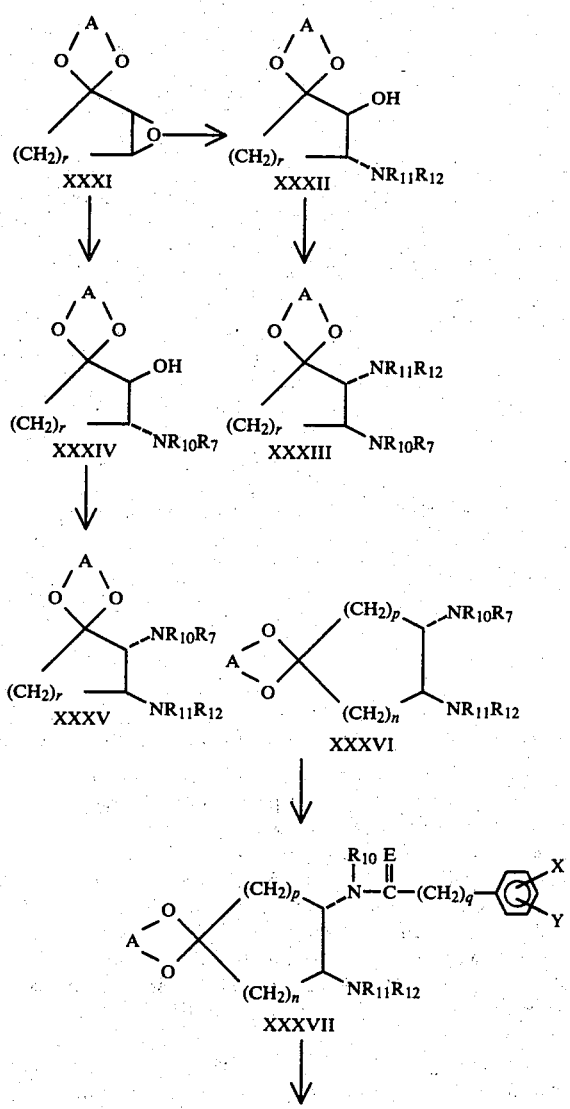

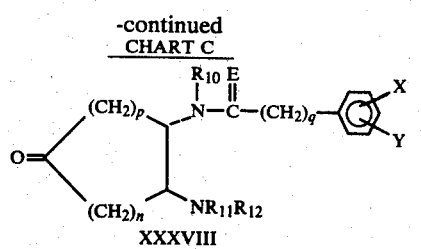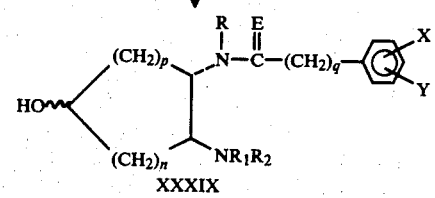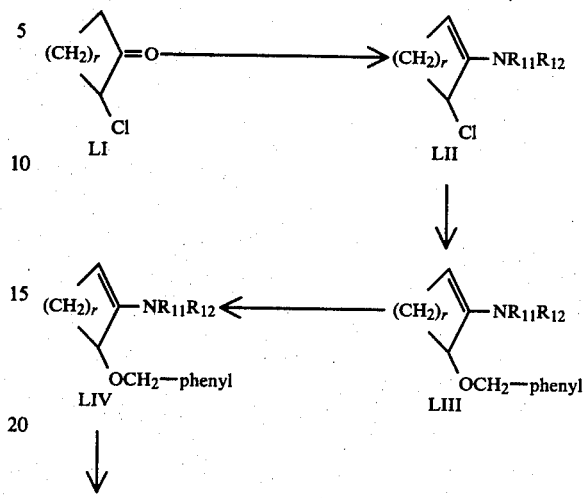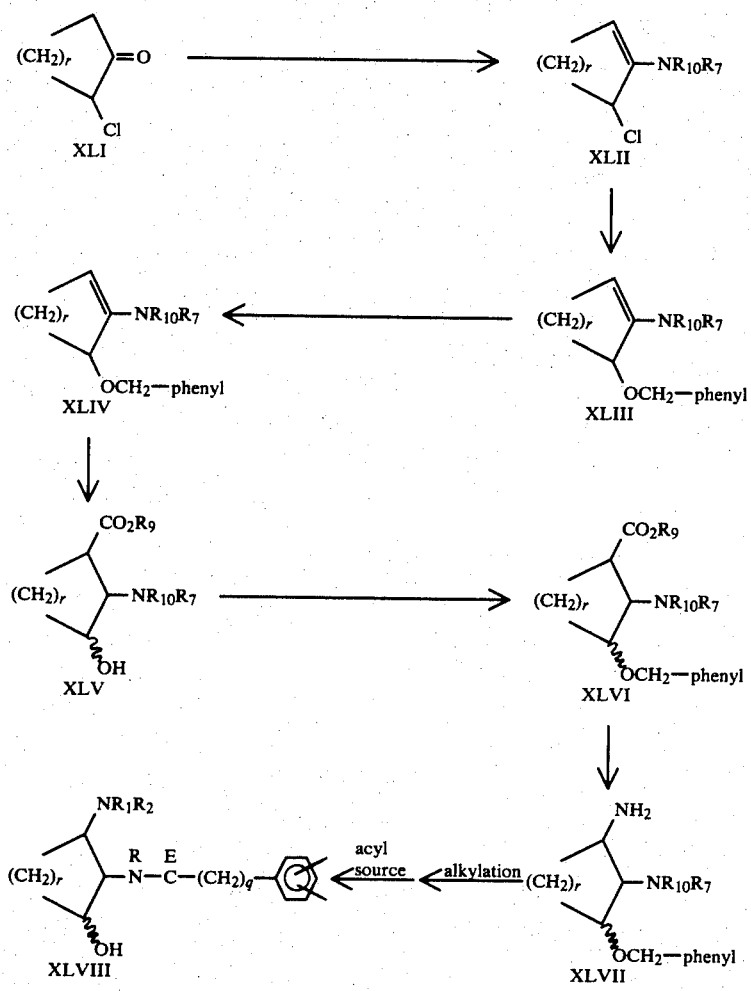

CHART E
(To prepare cis amino amides wherein n is zero)
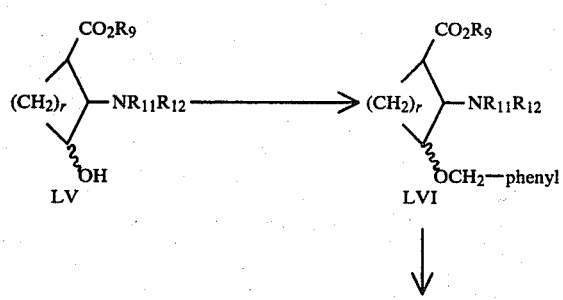
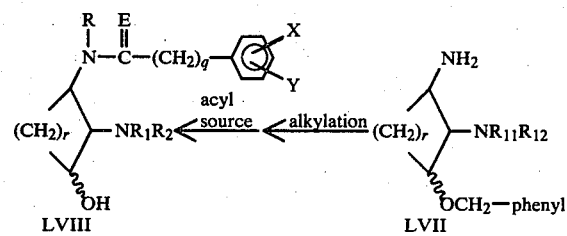
CHART F
(To prepare ketals wherein p is zero)
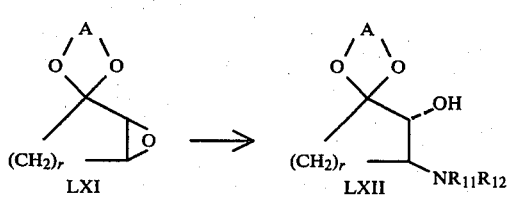
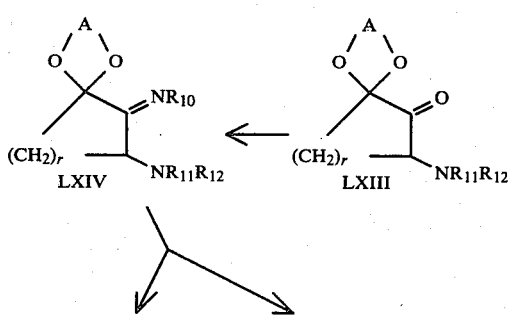
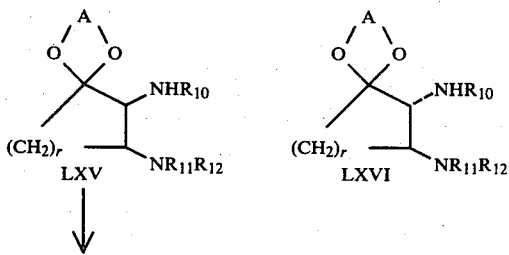
CHART F
(To prepare ketals wherein p is zero)
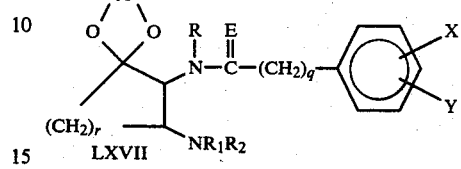
CHART G
(To prepare ketals wherein n is zero)
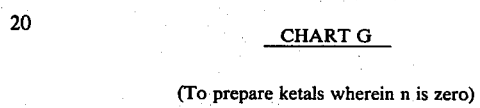
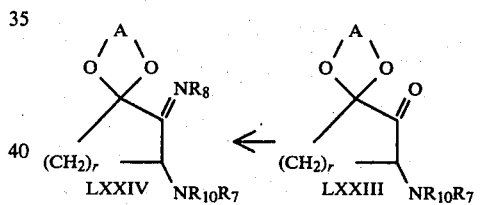
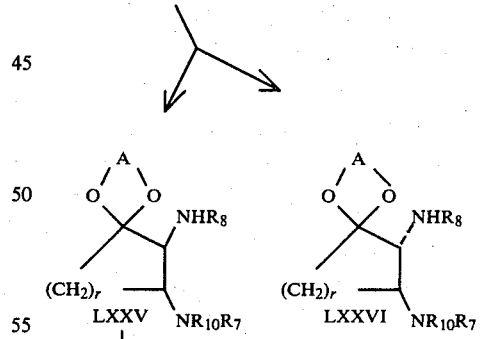
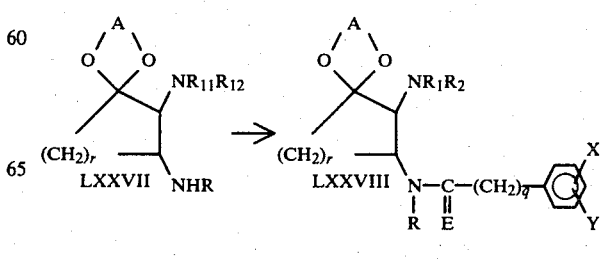

CHART H
(To prepare cis amino amides wherein p is zero)
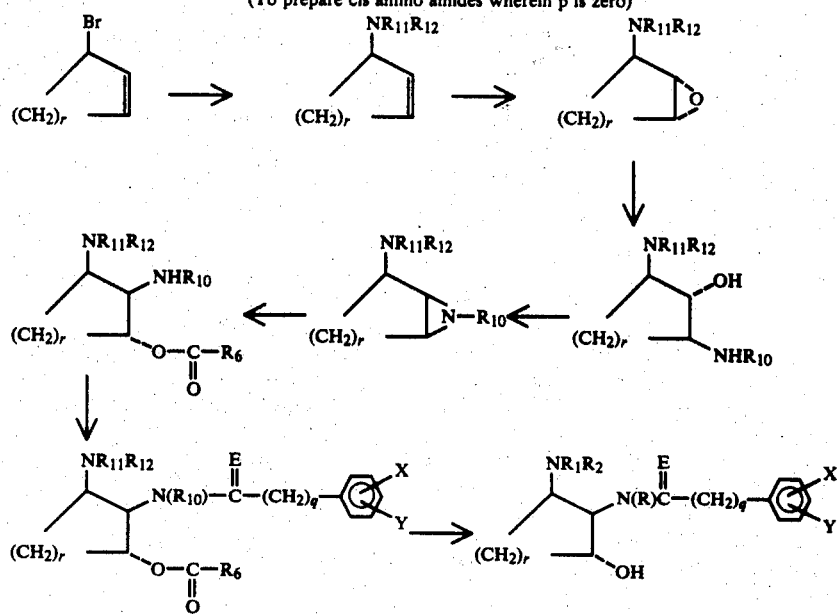
CHART I
(To prepare cis amino amides wherein n is zero)
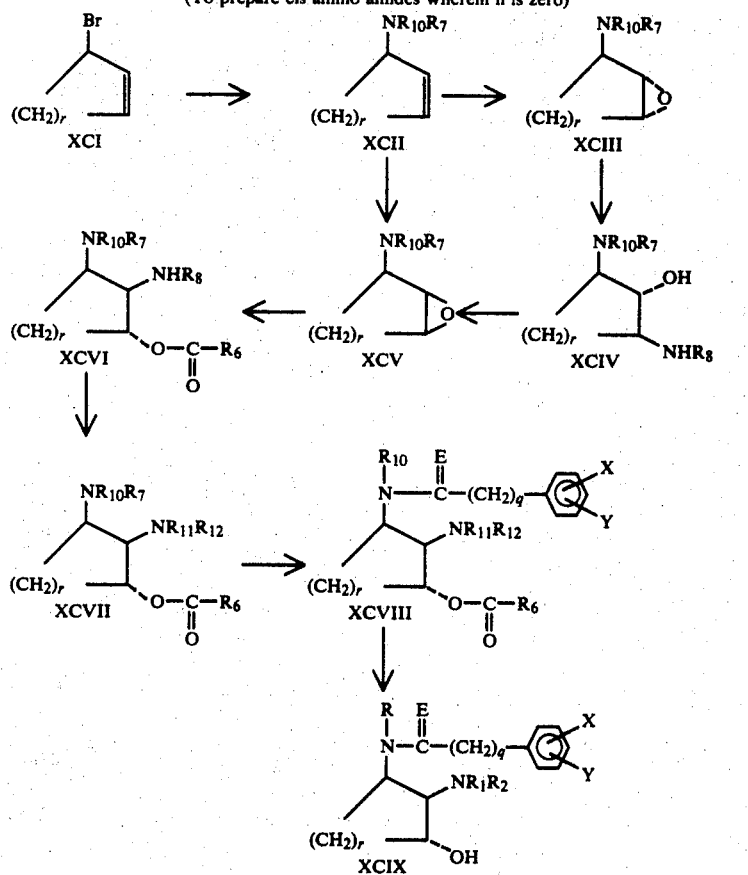
We claim:
1. A compound of the formula

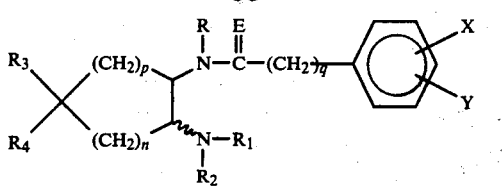

wherein:
R is hydrogen or $C_1$ to $C_3$-alkyl;
$R_1$ and $R_2$, taken separately, are each hydrogen or $C_1$ to $C_3$-alkyl;
$R_1$ and $R_2$, taken together with the nitrogen to which they are bonded, are azetidinyl, pyrrolidinyl or piperidinyl;
$R_3$, taken separately, is hydroxy, $C_1$ to $C_2$-alkyloxy, or $C_1$ to $C_3$-alkanoyloxy;
$R_4$, taken separately, is hydrogen when $R_3$ is hydroxy, $C_1$ to $C_2$-alkyloxy, or $C_1$ to $C_3$-alkanoyloxy;
$R_3$ and $R_4$, taken together, complete a moiety selected from the group, =G (oxo or thioxo), —G—$CH_2$—$H_2$—G—, —G—$CH_2CH_2CH_2$—G—, —G—$CH_2CH(CH_3)CH_2$—G—, —G—$CH_2C(CH_3)_2CH_2$—G—, wherein both G moieties in the same group are oxygen or bivalent sulfur, =N~OH, and =N~OC(=O)$CH_3$, wherein each G is oxygen or bivalent sulfur;
X and Y are independently selected from the group consisting of hydrogen, a halogen having an atomic number from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxacylamino(—NHC(=O)$R_6$, wherein $R_6$ is hydrogen or $C_1$ to $C_2$-alkyl);
p and n are whole number integers selected from the group zero, 2, 3, or 4 such that one of p and n is zero and the other of p and n is 2, 3, or 4;
q is zero or 1;
E is oxygen or bivalent sulfur;
provided that when R is $C_1$ to $C_3$-alkyl, $R_1$ and $R_2$ taken together with the nitrogen to which they are bonded complete a pyrrolidinyl ring, p is 3 and n is 0, q is 1, X and Y are chlorine in the 3 and 4 positions, $R_3$ is not hydroxy, $C_1$ to $C_2$-alkoxy or $C_1$ to $C_3$-alkanoyloxy;
or a pharmaceutically acceptable salt thereof.

2. A compound according to claim 1, wherein
R is $C_1$ to $C_3$-alkyl;
$R_1$ and $R_2$ are taken together with the nitrogen to which they are bonded to complete an N-pyrrolidinyl ring;
$R_3$ is methoxy;
$R_4$ is hydrogen;
X is hydrogen;
Y is a halogen having an atomic number of from 9 to 35;
p is 3;
n is 0;
q is 0;
E is oxygen;
or a pharmaceutically acceptable salt thereof.

3. A compound according to claim 2, wherein the compound is (1α,2β,3β)-4-bromo-N-[3-methoxy-2-(1-pyrrolidinyl)cyclohexyl]-N-methylbenzamide, or a pharmaceutically acceptable salt thereof.

4. A compound according to claim 2, wherein the compound is (1α,2β,3α)-4-bromo-N-[3-methoxy-2-(1-pyrrolidinyl)cyclohexyl]-N-methylbenzamide, or a pharmaceutically acceptable salt thereof.

5. A compound according to claim 1, wherein
R is $C_1$ to $C_3$-alkyl;
$R_1$ and $R_2$ are taken together with the nitrogen to which they are bonded to complete an N-pyrrolidinyl ring;
$R_3$ and $R_4$ are taken together to complete an ethylenedioxy ketal ring;
X and Y are each halogen having an atomic number of from 9 to 35;
p is zero;
n is 3;
q is 1;
E is oxygen;
or a pharmaceutically acceptable salt thereof.

6. A compound according to claim 5, wherein the compound is trans-3,4-dichloro-N-methyl-N-[7-(1-pyrrolidinyl)-1,4-dioxaspiro[4.5]dec-6-yl]benzeneacetamide,
or a pharmaceutically acceptable salt thereof.

7. A compound according to claim 1, wherein
R is $C_1$ to $C_3$-alkyl;
$R_1$ and $R_2$ are each $C_1$ to $C_3$-alkyl;
$R_3$ and $R_4$ are taken together to complete an ethylenedioxy ketal group;
X is hydrogen;
Y is a halogen having an atomic number of from 9 to 35;
p is 0;
n is 3;
q is 0;
E is oxygen;
or a pharmaceutically acceptable salt thereof.

8. A compound according to claim 7, wherein the compound is trans-4-bromo-N-[7-(dimethylamino)-1,4-dioxaspiro[4.5]dec-6-yl]-N-methylbenzamide,
or a pharmaceutically acceptable salt thereof.

9. A compound according to claim 7, wherein
R is $C_1$ to $C_3$-alkyl;
$R_1$ and $R_2$ are each $C_1$ to $C_3$-alkyl;
$R_3$ and $R_4$ are taken together to denote an ethylenedioxy ketal group;
X and Y are each halogen atoms having an atomic number of from 9 to 35;
p is 0;
n is 3;
q is 1;
E is oxygen;
or a pharmaceutically acceptable salt thereof.

10. A compound according to claim 9, wherein the compound is trans-3,4-dichloro-N-[7-(dimethylamino)-1,4-dioxaspiro[4.5]dec-6-yl]-N-methylbenzeneacetamide,
or a pharmaceutically acceptable salt thereof.

11. A compound according to claim 1, wherein
R is $C_1$ to $C_3$-alkyl;
$R_1$ and $R_2$ are taken together with the nitrogen to which they are attached to complete an N-pyrrolidinyl ring;
$R_3$ and $R_4$ are taken together to complete an ethylenedioxy ring;
X is a halogen having an atomic number of from 9 to 35 on the 4-position;
Y is hydrogen;
p is 3;
n is 0;
q is 0;

E is oxygen;
or a pharmaceutically acceptable salt thereof.

12. A compound according to claim 11, wherein the compound is 4-bromo-N-methyl-N-[6-(1-pyrrolidinyl)-1,4-dioxaspiro[4.5]dec-7-yl]benzamide;
or a pharmaceutically acceptable salt thereof.

13. A compound according to claim 1, wherein
R is $C_1$ to $C_3$-alkyl;
$R_1$ and $R_2$ are taken together with the nitrogen to which they are bonded to complete an N-pyrrolidinyl ring;
$R_3$ and $R_4$ are taken together to denote an oxo function;
X is a halogen having an atomic number of from 9 to 35 in the 4-position;
Y is hydrogen;
p is 3;
n is 0;
q is 0;
E is oxygen;
or a pharmaceutically acceptable salt thereof.

14. A compound according to claim 13, wherein the compound is 4-bromo-N-methyl-N-[3-oxo-2-(1-pyrrolidinyl)cyclohexyl]benzamide,
or a pharmaceutically acceptable salt thereof.

15. A compound according to claim 1 wherein the compound is selected from the group consisting of
4-bromo-N-[3-hydroxy-2-(1-pyrrolidinyl)cyclohexyl]-N-methylbenzamide,
4-bromo-N-methyl-N-[7-(1-pyrrolidinyl)-1,4-dioxaspiro[4.5]dec-6-yl]benzamide,
4-bromo-N-[2-hydroxy-6-(1-pyrrolidinyl)cyclohexyl]-N-methylbenzamide,
or a pharmaceutically acceptable salt thereof.

16. A composition useful in pharmaceutically effective dosage unit form for alleviating pain in warm blooded mammals which comprises a compound of claim 1 in combination with a pharmaceutically acceptable carrier.

17. A composition of claim 16 wherein the compound of claim 1 is a compound of the formula

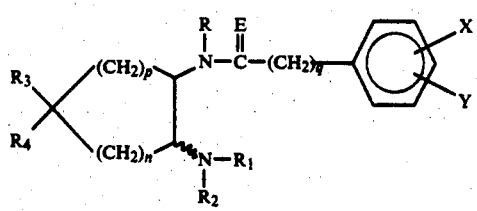

wherein
R is $C_1$ to $C_3$-alkyl;
$R_1$ and $R_2$ are taken together with the nitrogen to which they are bonded to complete an N-pyrrolidinyl ring;
$R_3$ and $R_4$ are taken together to complete an ethylenedioxy ketal ring;
X and Y are each halogen having an atomic number of from 9 to 35;
p is zero;
n is 3;
q is 1;
E is oxygen;
or a pharmaceutically acceptable salt thereof.

18. A composition of claim 17 wherein the compound of claim 1 is trans-3,4-dichloro-N-methyl-N-[7-(1-pyrrolidinyl)-1,4-dioxaspiro[4.5]dec-6-yl]benzeneacetamide, or a pharmaceutically acceptable salt thereof.

19. A method for alleviating pain which comprises administering to an animal suffering pain an effective amount of a compound of claim 1 in a pharmaceutical dosage unit form.

20. A method of claim 19 wherein the compound of claim 1 is trans-3,4-dichloro-N-methyl-N-[7-(1-pyrrolidinyl)-1,4-dioxaspiro[4.5]dec-6-yl]benzeneacetamide, or a pharmaceutically acceptable salt thereof.

* * * * *

UNITED STATES PATENT OFFICE
CERTIFICATE OF CORRECTION

Patent No. 4,359,476                    Dated November 16, 1982

Inventor(s) Lester J. Kaplan, Moses W. McMillan and Jacob Szmuszkovicz

It is certified that error appears in the above-identified patent and that said Letters Patent are hereby corrected as shown below:

Column 3, line 3: "-GH$_2$-Ch$_2$-CH$_2$-G" should read -- G-CH$_2$-CH$_2$-CH$_2$-G --.
Column 5, line 17: "undec-6-yl)" should read -- undec-6-yl] --.
Column 5, line 46: "E, Z and" should read -- E, X and ---.
Column 13, line 46: "making ue of" should read -- making use of --.
Column 16, line 13: "methaol" should read -- methanol --.
Column 16, line 26: "(1α,3β,6α)-" should read --A. (1α,3β,6α)- --.
Column 27, Chart B, Formula XXI should appear as follows instead of as in the patent:

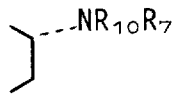

Column 32, Chart G, Formula LXXII should appear as follows instead of as in the patent:

Column 35, line 26: "=NH⌒OH ... =N⌒OC(=O)CH$_3$" should read -- =N⌒OH ... =N⌒OC(=O)CH$_3$ --.

Signed and Sealed this

Seventh Day of June 1983

[SEAL]

Attest:

DONALD J. QUIGG

Attesting Officer        Acting Commissioner of Patents and Trademarks